(12) United States Patent
Gupta et al.

(10) Patent No.: US 11,447,534 B2
(45) Date of Patent: Sep. 20, 2022

(54) PEPTIDE COMPLEX WITH IMMUNODULATORY AND ANTI-INFLAMMATORY FUNCTION

(71) Applicant: NATIONAL INSTITUTE OF IMMUNOLOGY, New Delhi (IN)

(72) Inventors: Sarika Gupta, New Delhi (IN); Viji Vijayan, New Delhi (IN)

(73) Assignee: NATIONAL INSTITUTE OF IMMUNOLOGY, New Delhi (IN)

( * ) Notice: Subject to any disclaimer, the term of this patent is extended or adjusted under 35 U.S.C. 154(b) by 0 days.

(21) Appl. No.: 17/051,259

(22) PCT Filed: Apr. 29, 2019

(86) PCT No.: PCT/IN2019/050343
§ 371 (c)(1),
(2) Date: Oct. 28, 2020

(87) PCT Pub. No.: WO2019/211865
PCT Pub. Date: Nov. 7, 2019

(65) Prior Publication Data
US 2021/0230244 A1    Jul. 29, 2021

(30) Foreign Application Priority Data
Apr. 30, 2018 (IN) .............................. 201811016307

(51) Int. Cl.
*A61K 38/00* (2006.01)
*C07K 14/575* (2006.01)
*A61P 29/00* (2006.01)
*C07K 14/47* (2006.01)

(52) U.S. Cl.
CPC ............ *C07K 14/575* (2013.01); *A61K 38/00* (2013.01); *A61P 29/00* (2018.01); *C07K 14/4711* (2013.01)

(58) Field of Classification Search
CPC ......... A61K 38/00; A61K 39/00; A61P 29/00; C07K 14/4711; C07K 14/575; C07K 14/00
See application file for complete search history.

(56) References Cited

FOREIGN PATENT DOCUMENTS

| CA | 2814737 A1 | 12/2001 | |
|---|---|---|---|
| WO | 2006/103116 A1 | 10/2006 | |
| WO | 2008/033518 A2 | 3/2008 | |
| WO | WO-2013059322 A2 * | 4/2013 | ......... A61K 38/1716 |

* cited by examiner

*Primary Examiner* — Aradhana Sasan
*Assistant Examiner* — Mercy H Sabila
(74) *Attorney, Agent, or Firm* — Jeffrey N. Townes; Cozen O'Connor

(57) ABSTRACT

The present invention relates to compositions that are effective in management of inflammatory diseases. The disclosure provides a peptide complex comprising Abeta 1-42 and undercarboxylated osteocalcin which displays anti-inflammatory and immunomodulatory functions. The disclosure further provides with processes for preparing the compositions.

Figure 1:
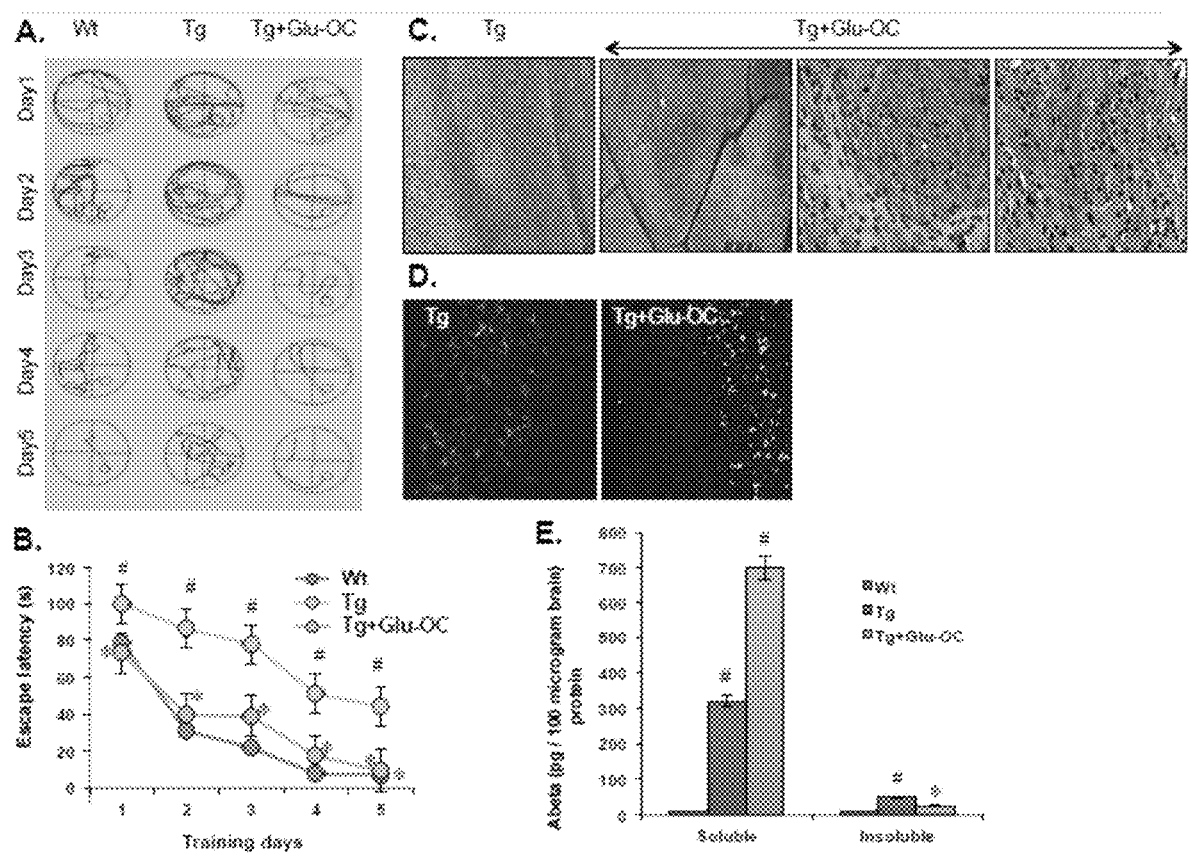

11 Claims, 10 Drawing Sheets
Specification includes a Sequence Listing.

PEPTIDE COMPLEX WITH IMMUNODULATORY AND ANTI-INFLAMMATORY FUNCTION

CROSS-REFERENCE TO RELATED APPLICATIONS

This application is a 371 national-stage application of International PCT Application No. PCT/IN2019/050343, filed Apr. 29, 2019, which claims priority to Indian Patent Application No. 201811016307, filed Apr. 30, 2018, both of which are incorporated herein by reference in their entirety.

FIELD OF INVENTION

The present disclosure relates to a peptide complex and use of the peptide complex for immunomodulation and treatment of inflammatory diseases.

BACKGROUND OF INVENTION

Anti-inflammatory drugs have improved the quality of life significantly and managed the progression of various diseases. Examples include aspirin, indomethacin, ibuprofen, celecoxib, ketoprofen etc. Currently both steroidal and non-steroidal anti-inflammatory drugs are used for the management of diseases. The combined analgesic, anti-inflammatory and antipyretic effects makes non-steroidal drugs useful for symptomatic relief of both pain and fever. Both classes of drugs are avoided for long term treatment owing to the severe gastrointestinal, cardiovascular, neurological and renal problems it produces [Tomic M, Micov A, Pecikoza U, Stepanovic-Paetrovic. Microsized and nanosized carriers for nonsteroidal antiinflammatory drugs: Formulations challenges and potential benefits. Chapter 1—clinical uses of non-steroidal anti-inflammatory drugs and potential benefits of NSAIDS modified release preparations. 2017; 1-29]. Thus, the safety and tolerability concerns associated with the use of anti-inflammatory agents continue to be an issue for both clinicians and patients.

Inflammation is a non-specific response of tissues to various insults that results in the release of a variety of materials at the site of inflammation and development of pain. The process involves many cell types like lymphocytes, macrophages, neutrophils, mast cells and immune cells. Amongst these, macrophages that represent closely related cells of bone marrow origin, like blood monocytes, and tissue macrophages have diverse roles to play during an inflammation like (a.) antigen presentation, (b.) phagocytosis and (c.) immunomodulation making these cell types an important target for treatment of various diseases involving inflammation [Fujiwara N, Kobayashi K, Macrophages in inflammation. 2005; 4: 281-286].

Activated macrophages exist as two types: (a.) 'the classically activated macrophages' exhibit a Th1-like phenotype, promoting inflammation, extracellular matrix destruction and apoptosis. The ligands after binding and recognition via molecules like CD14 receptor and TLR or toll like receptors, are phagocytosed and delivered to lysosomes for degradation. This type of activation requires priming. Thereafter, the antigens are processed, loaded onto class II major histocompatibility complex (MHC-II) in the late endosomes and presented to T cells. The macrophages herein this function as antigen processing cells or APC. These also produce mediators like chemokines eg. IL-8, IP-10, MIP-1 alpha, RANTES, pro-inflammatory mediators like interleukin 1beta, interleukin-6, tumour necrosis factor-alpha, nitric oxide (due to inducible nitric oxide synthase upregulation), proteolytic enzymes like matrix metalloproteinases or MMPs like MMP-2, -7, -9 and -12 which degrade extracellular matrix components and produce collateral damage to tissues to induce disorders like cancer, type 1 autoimmune disorders and glomerulonephritis. (b.) 'The alternatively activated macrophages' on the other hand display a Th2-like phenotype and do not require priming. Mediators like interleukin-4, interleukin-13 are sufficient for induction. These, facilitate fluid phase pinocytosis of soluble antigen, which are processed, loaded onto class II MHC molecules and presented to T cells. The alternatively activated macrophages promote ECM construction, cell proliferation, angiogenesis, wound healing and resolution of inflammation.

The above-mentioned facts demonstrate that inflammation is a very complicated process and cautious therapeutic methods ought to be taken to resolve inflammation since inflammatory cells like macrophages needs to be modulated depending upon the milieu for resolution of inflammation and not directly inhibited.

In the last several years, peptide therapeutics have gained wide attention. More than 60 peptide drugs have reached the market as therapeutic peptides, out of which few are in preclinical and clinical development. Peptides represent a unique class of pharmaceutical compounds, molecularly positioned between small molecules and proteins, yet biochemically and therapeutically unique from both. They serve as intrinsic signaling molecules for many physiological functions and thus provide an opportunity for therapeutic intervention that mimics natural pathways. The first therapeutic peptide insulin was administered to diabetic patients in 1920s who did not synthesize sufficient insulin. Apart from insulin, adrenocorticotropic hormone or ACTH, calcitonin, oxytocin, vasopressin, octreotide, leuprorelin were introduced from 1950s onwards. The evolution of peptide therapeutics, a dataset of therapeutic peptides, development status of peptide therapeutics, physical characteristics of peptide therapeutics and clinical developmental timelines can be seen detailed in a review by Lau and Dunn, 2017 [Lau J L, Dunn M K. Therapeutic peptides: Historical perspectives, current development trends and future directions. Bioorganic and Medicinal Chemistry. 2017; In Press].

Some of the key features of peptides are their specificity, potency, predicted metabolism and safe mode of action. The production cost of peptide therapeutics is also lower. Details of peptide therapeutics used today as medications and the future of these multi-functional molecular medicines is available as a review in Drug Discovery Today, 2015 [Fosgerau K, Hoffmann T. Peptide therapeutics: current status and future directions. Drug Discovery Today. 2015; 20: 122-128].

Peptides also have immunomodulatory functions. Immunomodulatory agents have become an important drug category to treat inflammation—since it is the underlying basis of any disease. Immunomodulatory agents work by different mechanisms like apoptosis and cell cycle arrest, inhibition of interaction of inflammatory cells to microenvironment where the inflammation is mediated, inhibition of cytokine production and regulation of T cells and natural killer cells [Reske T, Fulciniti M, Munshi N C, Mechanism of action of immunomodulatory agents in multiple myeloma. Med Oncol. 2010; 27: S7-13]. Pexiganan acetate, omiganan, hLF1-11, iseganan, PAC-113, IMX942, OP-145 and plectasin are some of the immunomodulatory peptides in clinical trials. Ideally, the peptides with the greatest pharmaceutical potential are those that possess immunomodulatory functions. Challenges and strategies that are used to optimize peptides for clinical use are mentioned in the review in Biopolymers, 2013 [Haney E F, Hancock E W. Peptide design for anti-microbial and immunomodulatory applications. Biopolymers. 2013; 100: 572-583].

During a therapeutic regimen involving biologically active peptides to reduce amyloidosis in 5×FAD transgenic (Tg) Alzheimer mouse model, we discovered that certain immunomodulatory complexes get formed in the brain of mice. Herein we administered 300 ng of undercarboxylated osteocalcin or Glu-OC to 5×FAD Tg mouse for 60 days and found co-localization of "Abeta42" with "osteocalcin". We comprehended that these were associated with microglial activation that was otherwise absent in 5×FAD Tg control mice. The interaction of Abeta42 and Glu-OC was facilitated in situ and tested for immunomodulatory potential. The complex demonstrated immunomodulatory potential and hence this invention herein is described. We envisage this complex with its immunomodulatory and anti-inflammatory potential will have commercial application for the treatment of immune and inflammatory disorders.

Osteocalcin is a non-collagenous protein found associated with the bone matrix. It name comes from both Greek and Latin. 'Osteo' is Greek term for bone and 'Calc' is a Latin term for lime salts. Osteocalcin is primarily synthesized by osteoblasts and ondontoblasts and comprises 15 to 20% of the non-collagenous protein of bone.

Osteocalcin is synthesized as a pre-pro-molecule and undergoes cleavage to form a 49 amino acid residue length that contains 3 glutamic acid residues in its primary structure. Mature human osteocalcin has a predicted molecular mass of 5,800 kDa [Poser et al., 1980, J Biol Chem. 255:8685-8691]. When the 3 glutamic acid residues of osteocalcin are carboxylated by carboxylase though a vitamin K-dependent mechanism], the peptide is referred to as carboxylated osteocalcin or Gla-OC. The carboxylated Gla residues are found at positions 17, 21 and 24 in mature human osteocalcin [Poser et al., 1980, J. Biol. Chem. 255:8685-8691]. Gla-OC has a negative charge and binds $Ca^2$ in hydroxyapatite [Hauschka et al., 1989, Physiol. Review 69:990-1047].

When uncarboxylated, osteocalcin is referred to as uncarboxylated or undercarboxylated osteocalcin or Glu-OC. Since it is under carboxylated, it has low affinity for hydroxyapatite and thus majorly found in circulation. A series of experimental studies have shown that undercarboxylated osteocalcin has endocrine role. It regulates energy expenditure, increases insulin sensitivity of peripheral tissues and stimulates insulin secretion by pancreatic β-cells, adiponectin release by adipocytes and testosterone synthesis in Leydig cells [Garcia-Martin A, Reyes-Garcia, Avila-Rubio V, Munoz-Torres M, Osteocalcin: a link between bone homeostasis and energy metabolism. Endocrinol. Nutr. 2013; 60: 260-263; Wei J, Hanna T, Suda N, Karsenty G, Ducy P. Osteocalcin promotes β-cell proliferation during development and adulthood through Gprc6a. Diabetes. 2014; 63: 1021-1031; Oury F, Ferron M, Huizhen W, Confavreux C, Xu L, Lacombe J, Srinivas P, Chamouni A, Lugani F, Lejeune H, Kumar T R, Plotton I, Karsenty G. Osteocalcin regulates murine and human fertility through a pancreas-bone-testis axis. J. Clin. Invest. 2013; 123:2421-2433; Ferron M, Hinoi E, Karsenty G, Ducy P. Osteocalcin differentially regulates beta-cell and adipocyte gene expression and affects the development of metabolic diseases in wild-type mice. Proc. Natl. Acad. Sci. USA. 2008; 105: 5266-5270].

Osteocalcin crosses the blood-brain barrier, aids fetal brain development and improves cognitive function [Oury F, Khrimian L, Denny C A, Gardin A, Chamouni A, Goeden N, Huang Y, Lee H, Srinivas P, Gao X, Suyama S, Langer T, Mann J J, Horvath T L, Bonnin A, Karsenty G. Maternal and offspring pools of osteocalcin influence brain development and functions. Cell. 2013; 155:228-241; US2016004571A1].

Osteocalcin protects mice against high fat diet induced obesity and type 2 diabetes [Ferron M, McKee M D, Levine R L, Ducy P, Karsenty G. Intermittent injections of osteocalcin improve glucose metabolism and prevent type 2 diabetes in mice. Bone. 2012; 50:568-575; Lee N K, Sowa H, Hinoi E, Ferron M, Ahn J D, Confavreux C, Dacquin R, Mee P J, McKee M D, Jung D Y, Zhang Z, Kim J K, Mauvais-Jarvis F, Ducy P, Karsenty G. Endocrine regulation of energy metabolism by the skeleton. Cell. 2007; 130:456-469; Karsenty G, Ferron M. The contribution of bone to whole-organism physiology. Nature. 2012; 481: 314-320].

Amyloid beta denotes peptides of 36 to 43 amino acid length whose normal function is yet to be understood. Abeta peptide is derived by proteolytic processing of the amyloid precursor protein, a type I integral membrane protein. Foremost, APP is delivered to the plasma membrane where it is subjected to proteolytic processing by α-secretase. In the absence of α-secretase cleavage, APP molecules get internalized into endocytic compartments where these are subjected to cleaved by β-secretase (BACE) and γ-secretase to generate Abeta. The Golgi apparatus and to a lesser extent the endoplasmic reticulum are also sources of a distinct population of Abeta peptides secreted into the extracellular space. The majority of secreted A beta peptides are 40 amino acids in length (Abeta40), whereas a smaller fraction of Abeta is cleaved to produce a 42 amino acid species (Abeta42), is the main amyloid peptide that drives production of amyloid fibrils. Abeta42 may be degraded by proteases such as the insulin-degrading enzyme or neprilysin. Abeta generated from axon-transported APP is released from presynaptic sites and subsequently accumulates close to the nerve terminal.

The hydrophobicity of Abeta42 facilitates aggregation propensity. Naturally occurring Abeta can assemble in vivo into metastable dimers, trimers and oligomers at nanomolar concentrations. The soluble non-fibrillar forms of Abeta42 are considered more toxic than other forms. Most research have been done to know more about the function of Abeta42 owing to its association with amyloid plaques in brains of Alzheimer diseased patients. However, Abeta exists in normal individuals and low concentrations of Abeta play role in synaptic plasticity and neuronal survival. Other proposed functions of Abeta include memory consolidation, cholesterol transport and antioxidant functions. A patent by George-Hyslop, Fraser and Westaway describes that Abeta42 can reduce amyloid pathology in mice [Parihar M S, Brewer G J. Amyloid Abeta as a modulator of synaptic plasticity. J ALzheimers Dis; 22: 741-763; St. G, Fraser P E, Westaway D, Patent Application CA2814737A1].

SUMMARY OF INVENTION

In an aspect of the present disclosure, there is provided a peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2.

In an aspect of the present disclosure, there is provided a process for preparing a peptide complex comprising Abeta 1-42 peptide and undercarboxylated osteocalcin (Glu-OC), said process comprising: (a) obtaining undercarboxylated osteocalcin having an amino acid sequence as set forth in SEQ ID NO: 2; (b) obtaining Abeta 1-42 peptide having an amino acid sequence as set forth in SEQ ID NO: 1, and (c) contacting the undercarboxylated osteocalcin and the Abeta 1-42 peptide under suitable conditions to obtain the peptide complex.

In an aspect of the present disclosure, there is provided a method of treating a subject having inflammation, said method comprising, administering to the subject a therapeutically effective amount of a peptide complex comprising Abeta 1-42 peptide and undercarboxylated osteocalcin (Glu-OC), wherein Abeta 1-42 peptide is represented by SEQ ID NO: 1, and undercarboxylated osteocalcin is represented by SEQ ID NO: 2.

In an aspect of the present disclosure, there is provided a method of identifying a compound for modulating inflammation, said method comprising; (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation.

In an aspect of the present disclosure, there is provided a compound identified by a method comprising: (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation.

In an aspect of the present disclosure, there is provided a method of treating a subject having inflammation, said method comprising, administering to the subject a therapeutically effective amount of a compound identified by a method comprising: (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

FIGS. 1A and 1B depict the outcome of Morris Water Maze (MWM) test in untreated and treated 5×FAD Tg mice, in accordance with an embodiment of the present disclosure. Undercarboxylated osteocalcin or Glu-OC treated 5×FAD Tg mice showed lower escape latency as compared to 5×FAD Tg control which showed greater escape latency as compared to wild-type. The significance of the differences was evaluated by two-way ANOVA, followed by individual comparison using Bonferroni post test. Data are shown as mean±SEM, n=4 animals per group; #statistical significance with wild-type mice, *statistical significance with 5×FAD transgenic mice, P<0.05.

FIGS. 1C and 1D are visual representations of the brains of 5×FAD Tg mice before and after Glu-OC treatment, in accordance with an embodiment of the present disclosure. FIG. 1C depict Congo red stained microphotographs of brain sections under ordinary light. As shown, section of 5×FAD Tg control brain suffers significant amyloid deposition as evidenced by intense red stain. In Gla-OC treated 5×FAD Tg mice, the brain showed lesser amyloid deposits but these concentrated fibrillar structures. FIG. 1D is microphotograph of brain section immunostained with Abeta1-42 fibrillar specific antibody. As shown, brain from 5×FAD Tg mice treated with Glu-OC display fewer yet larger Abeta42+ fibrillar amyloid deposits.

FIG. 1E depict bar graphs showing the effect of Gla-OC treatment on soluble and insoluble Abeta42 in brain as evidenced by ELISA in accordance with an embodiment of the present disclosure. Though Gla-OC significantly reduced insoluble Abeta42 levels in 5×FAD Tg brain as compared to 5×FAD Tg mice, the treatment significantly increased the level of soluble Abeta42 in brain. The significance of the differences was evaluated by two-way ANOVA, followed by individual comparison using Bonferroni post test. Data are shown as mean±SEM, n=4 animals per group; #statistical significance with wild-type mice and *statistical significance with 5×FAD transgenic mice, P<0.05.

Figure 2:
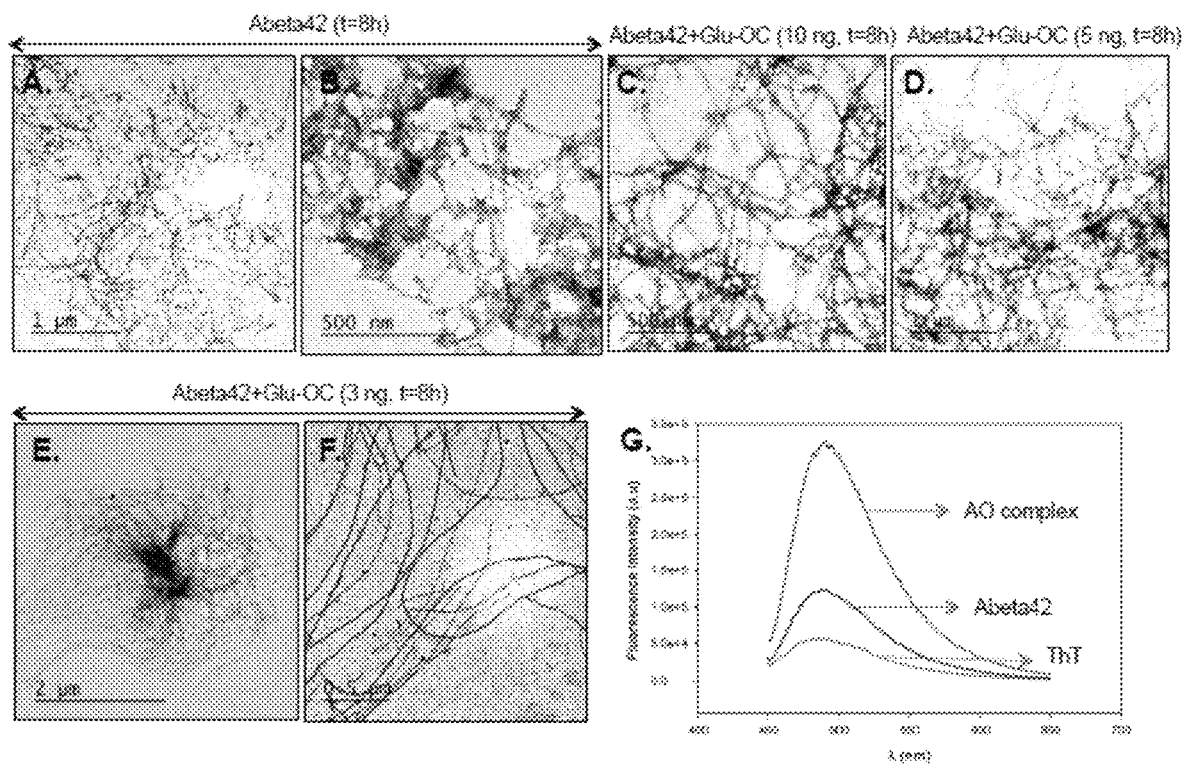

FIG. 2 demonstrates the effect of Glu-OC on Abeta42 fibrillization in situ in accordance with an embodiment of the present disclosure. FIG. 2A-2F are TEM images showing Abeta42 in the presence and absence of Gla-OC. FIGS. 2A and 2B are Abeta42 controls at a concentration of 100 micromolar kept for aggregation in 1×PBS (pH 7.4) at 37° C. for 8 hours. FIGS. 2C-2F are TEM images of Abeta 42 (100 micromolar) in the presence of different concentrations of Glu-OC (3 ng-10 ng) kept for aggregation in 1×PBS (pH 7.4) at 37° C. for 8 hours. FIG. 2G depicts a graph showing the fluorescence emission spectra of Abeta42 and Abeta42 with Glu-OC using ThT binding assay, in accordance with an embodiment of the present disclosure.

Figure 3:
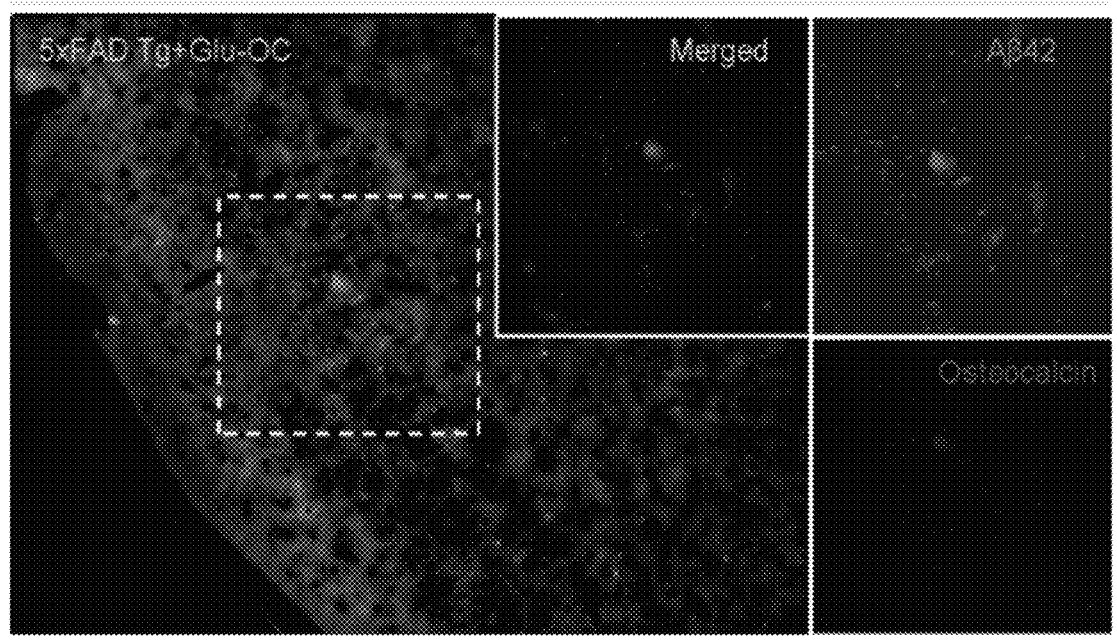

FIG. 3 is an immunohistochemical data of brain sections from Glu-OC treated 5×FAD mice showing co-localization of Abeta42 and osteocalcin (merged) in accordance with an embodiment of the present disclosure. Also shown are separate microphotographs of brain sections immunostained with Abeta42 and osteocalcin.

Figure 4:
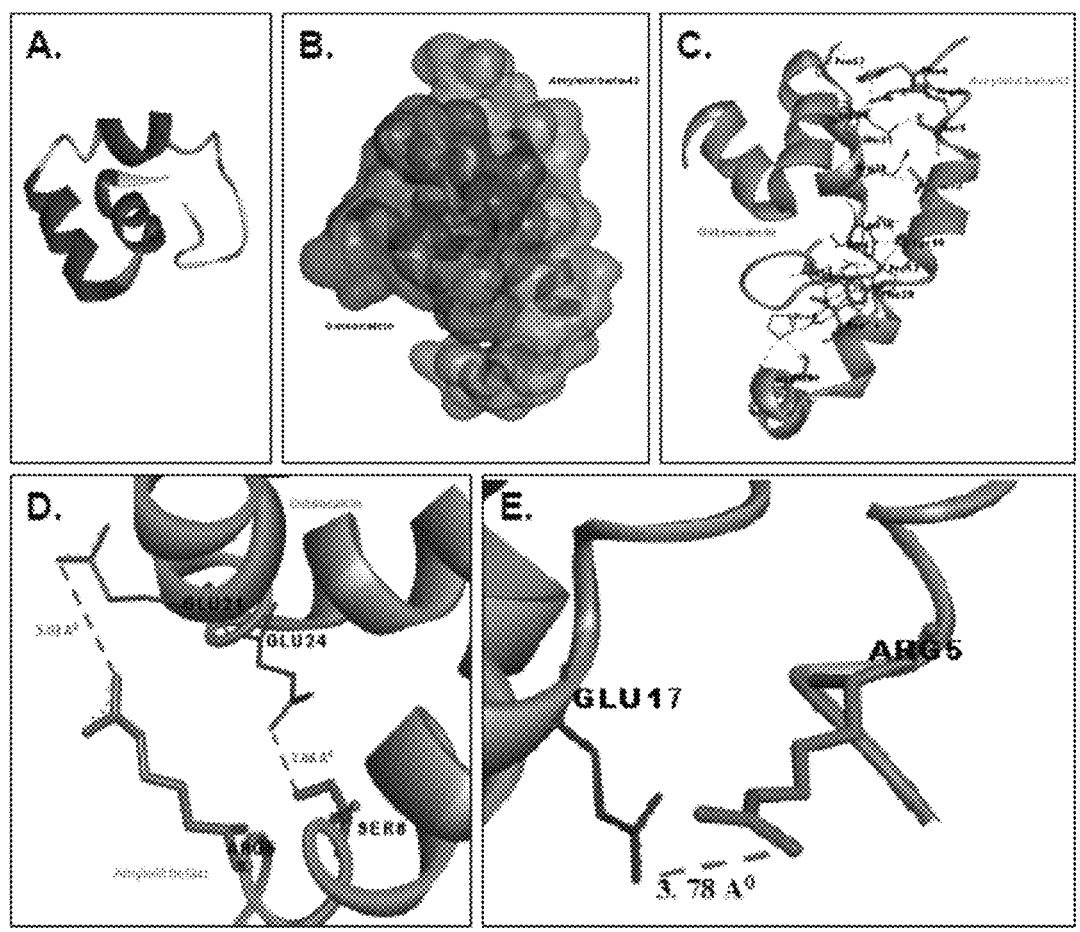

FIG. 4 depicts Abeta42 and Glu-OC interaction by bioinformatics tools in accordance with an embodiment of the present disclosure. FIG. 4A is predicted structure of osteocalcin. FIGS. 4B-4C represent docked images of monomeric structure of Abeta42 and ab initio predicted structure of osteocalcin. FIGS. 4D-4E represent interactions between Abeta42 and Glu-OC such as electrostatic interactions and hydrogen bonding predicted through Zdock and Patchdock servers.

Figure 5:
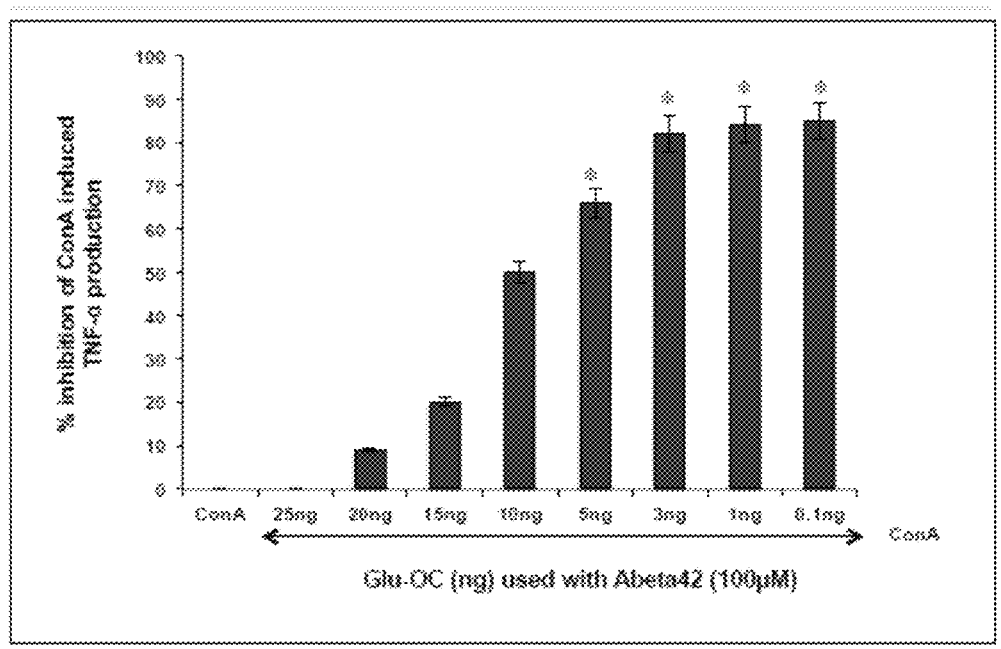

FIG. 5 demonstrates the percentage inhibition of ConcanavalinA (ConA) (5 microgram per ml) induced tumor necrosis factor-alpha (TNF-alpha) production in RAW 264.7 macrophages when exposed to mixtures containing different concentrations of Glu-OC (25 ng-0.1 ng) and Abeta42 (100 micromolar) in accordance with an embodiment of the present disclosure. Various concentrations of Glu-OC (25 ng-0.1 ng) were incubated with 100 micromolar concentration of Abeta 42 at 37° C. for 4 hours. The mixtures were preincubated with RAW264.7 macrophage cells ($2\times10^6$ cells) for 30 mins prior to ConA stimulation and TNF-alpha levels were evaluated by ELISA. Results are represented as % inhibition of ConA induced TNF-alpha. The significance of the differences was evaluated by two-way ANOVA, followed by individual comparison using Bonferroni post test. Data are shown as mean±SEM, n=4; *statistical significance with ConA control, P<0.05.

Figure 6:
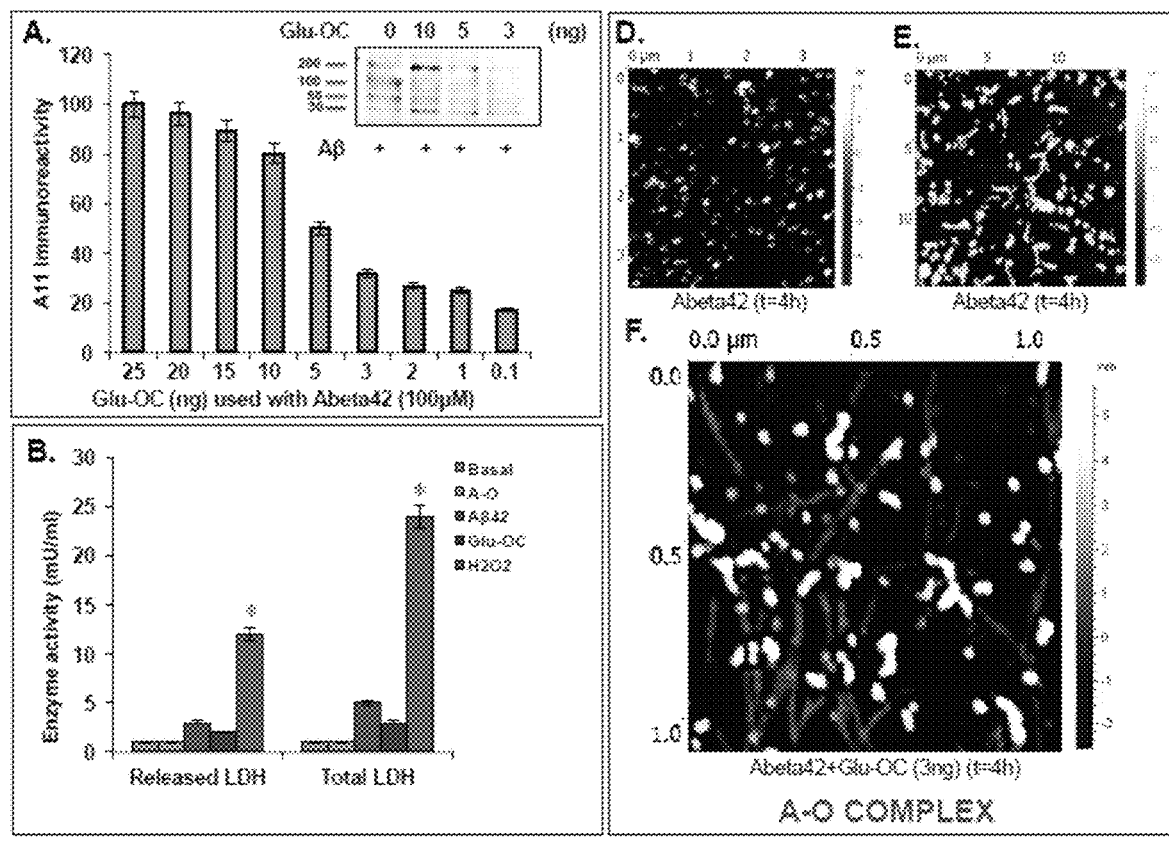

FIG. 6 demonstrates the formation of Glu-OC-Abeta42 complex in situ and development of A-O complex in accordance with an embodiment of the present disclosure. FIG. 6A represents bar diagram illustrating the immunoreactivity of various mixtures containing Glu-OC (25 ng-0.1 ng) and Abeta42 (100 micromolar) towards A11 antibody. FIG. 6A also displays a Western blot (FIG. 6C) showing the immunoreactivity of A11 towards selected Glu-OC-Abeta42 mixtures which demonstrates that Glu-OC-Abeta42 mixture containing 3 ng of osteocalcin (A-O complex) produces least reactivity with A11 and hence are non-toxic species. FIG. 6B is a bar diagram demonstrating that the lactate dehydrogenase (LDH) enzyme activity in RAW264.7 macrophage cultures when are exposed to Glu-OC-Abeta42 mixture containing 3 ng osteocalcin (A-O complex). $H_2O_2$ or hydrogen peroxide was used as positive control. FIGS. 6D-6F are AFM images illustrating the structures of Abeta42 and A-O complex. The significance of the differences was evaluated by two-way ANOVA, followed by individual comparison using Bonferroni post test. Data are shown as mean±SEM, n=4; *statistical significance with basal, P<0.05.

Figure 7:
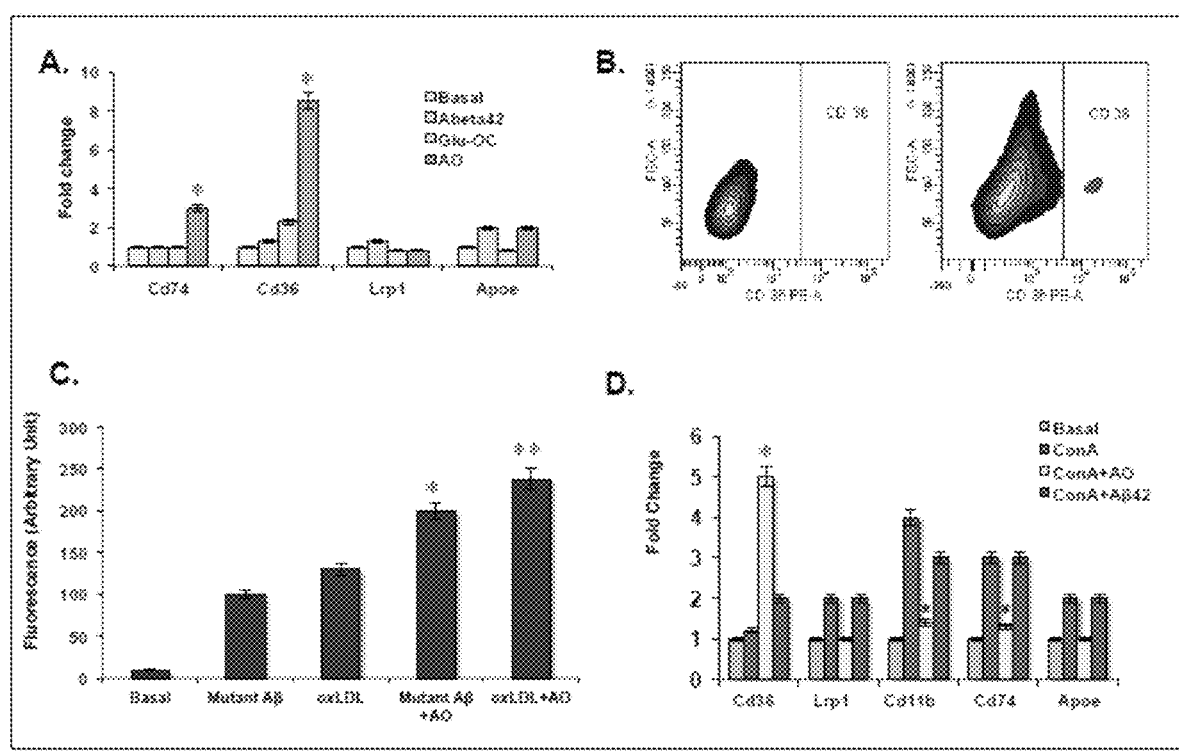

FIG. 7 demonstrates the immunomodulatory potential of A-O complex, in accordance with an embodiment of the present disclosure. FIG. 7A is a bar diagram demonstrating the fold changes in mRNA levels of Cd74 (MHC-II), Cd36, Lrp1 and Apoe genes in RAW264.7 macrophages when exposed to A-O complex (with respect to basal) as evidenced by qPCR. FIG. 7B is flow cytometric data showing the cell surface expression of CD36 scavenger receptor in macrophage cells after exposure to A-O complex. FIG. 7C depicts a bar diagram demonstrating the changes in the uptake of fluorescent tagged CD36 ligands like mutant Abeta42 and oxidized lipoprotein (oxLDL) by macrophages in the presence and absence of A-O complex as evidenced by FACS. FIG. 7D, represents a qPCR data showing fold changes in mRNA level of Cd36, Lrp1, Cd11b, Cd74 and Apoe in ConA stimulated macrophages in the presence and absence of A-O complex. The significance of the differences was evaluated by two-way ANOVA, followed by individual comparison using Bonferroni post test. Data are shown as mean±SEM, n=4. In FIG. 8A, *statistical significance with basal, P<0.05; In FIG. 7C, *statistical significance with mutant Abeta and **statistical significance with oxidized LDL or oxidized lipoprotein, P<0.05.

Figure 8:
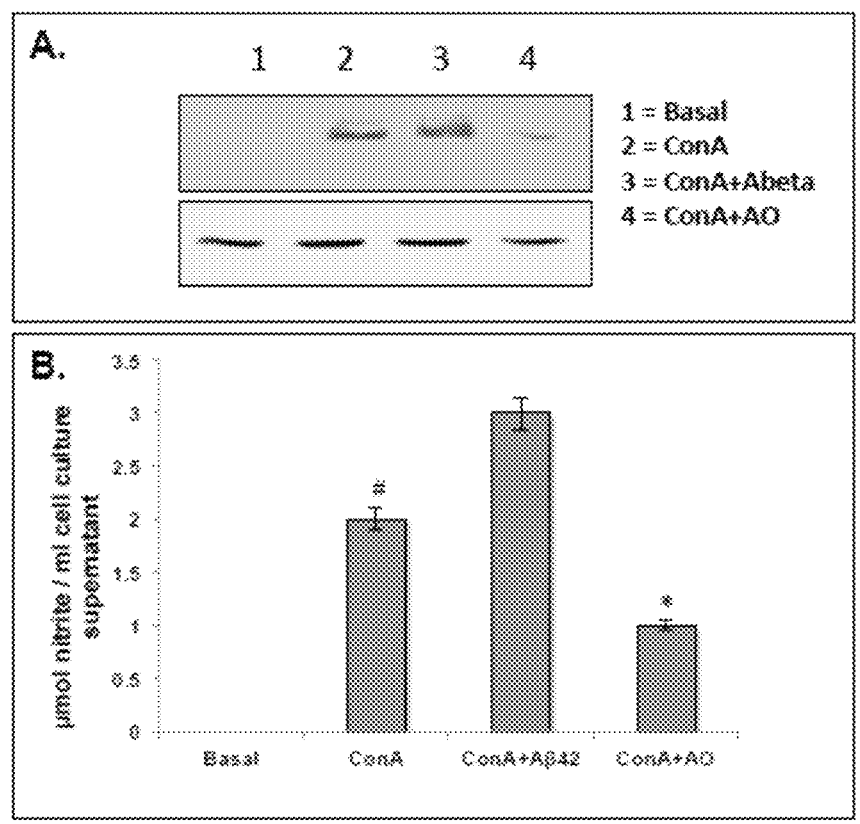

FIG. 8 demonstrates the anti-inflammatory potential of A-O complex, in accordance with an embodiment of the present disclosure. FIG. 8A is a representative Western blot image showing the inhibitory effect of A-O complex against ConA-induced nitric oxide synthase (iNOS) protein expression. FIG. 8B is a bar diagram depicting changes in nitrite level in ConA activated macrophages in presence or absence of A-O complex. The significance of the differences was evaluated by two-way ANOVA, followed by individual comparison using Bonferroni post test. Data are shown as mean±SEM, n=4; #statistical significance with basal; *statistical significance with basal P<0.05.

Figure 9:
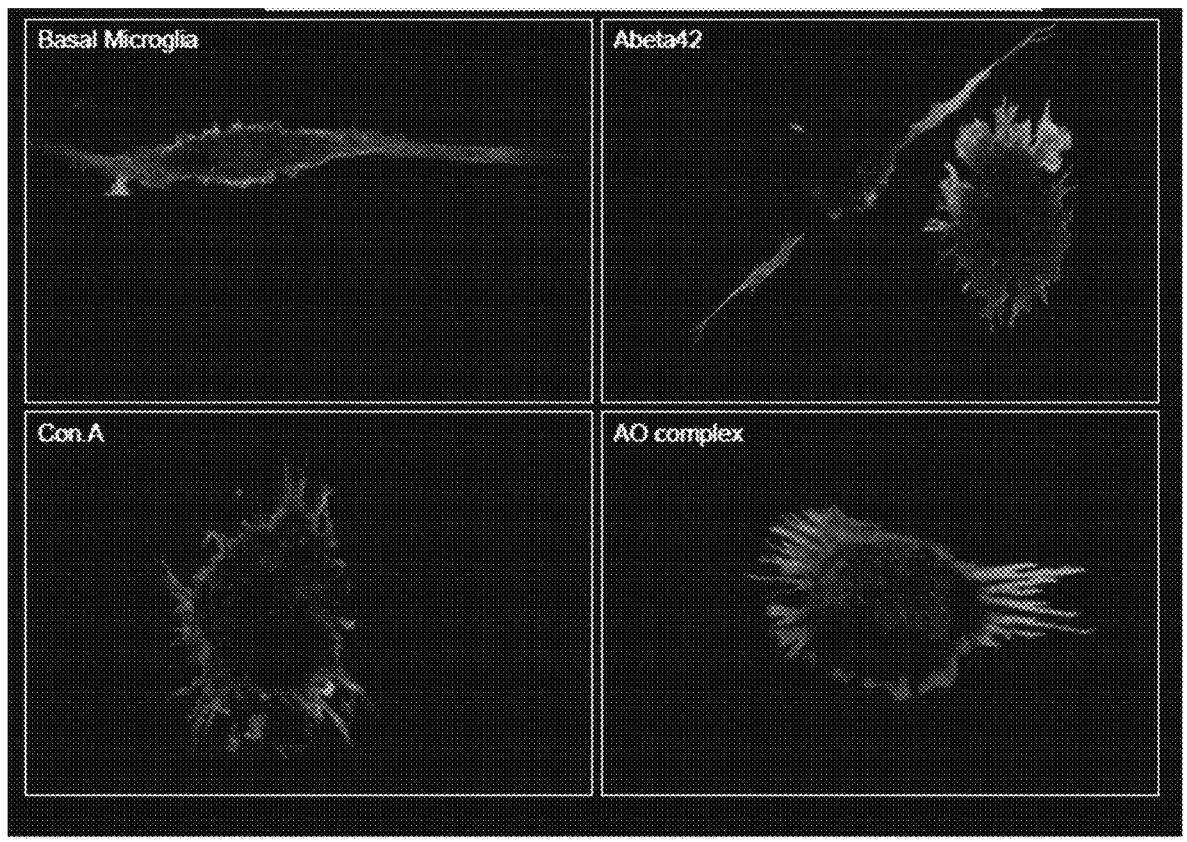

FIG. 9 represents a confocal microphotograph demonstrating F-actin changes in EOC20 microglia (brain macrophages) upon treatment with Abeta42, ConA and A-O complex, in accordance with an embodiment of the present disclosure.

Figure 10:
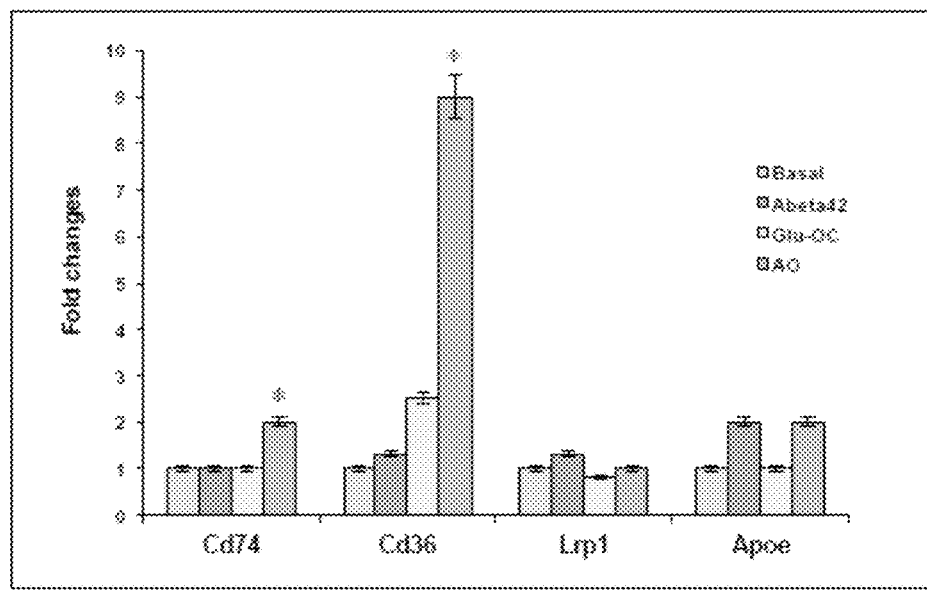

FIG. 10 demonstrates the effect of A-O complex on unstimulated microglia, in accordance with an embodiment of the present disclosure. The bar diagram depicts a qPCR data that shows the fold changes in mRNA levels of genes Cd74, Cd36, Lrp1 and Apoe after exposure to A-O complex as evidenced by qPCR. The significance of the differences was evaluated by two-way ANOVA, followed by individual comparison using Bonferroni post test. Data are shown as mean±SEM, n=4; *statistical significance with basal P<0.05.

Figure 11:
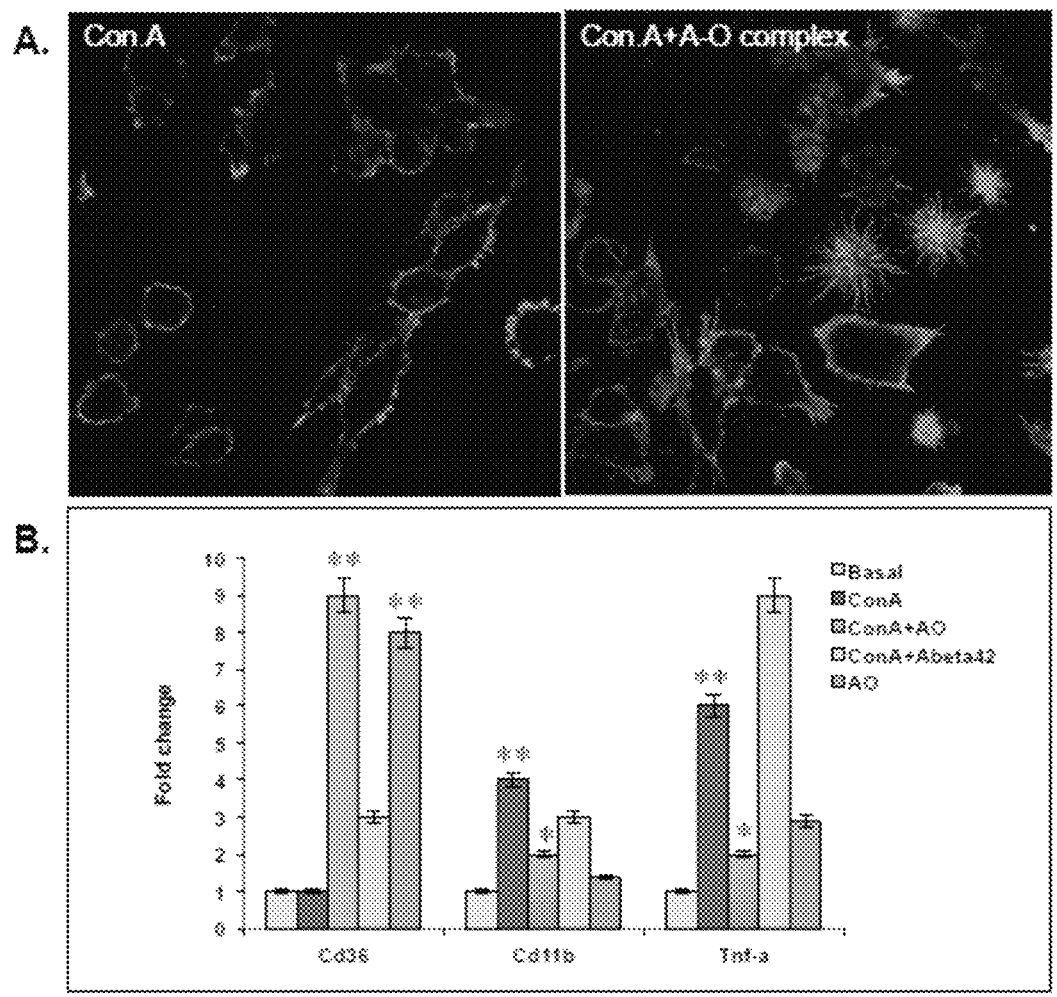

FIG. 11 demonstrates the effect of A-O complex on ConA stimulated microglia, in accordance with an embodiment of the present disclosure. FIG. 11A represents confocal microphotographs demonstrating F-actin changes in EOC20 microglia (brain macrophages) upon treatment with ConA and A-O complex. FIG. 11B is a bar diagram depicting fold changes in mRNA levels of genes Cd36, Cd11b and Tnf-a in ConA stimulated microglia with or without A-O complex exposure as evidenced by qPCR. The significance of the differences was evaluated by two-way ANOVA, followed by individual comparison using Bonferroni post test. Data are shown as mean±SEM, n=4; **statistical significance with basal, *statistical significance with ConA P<0.05.

Figure 12:
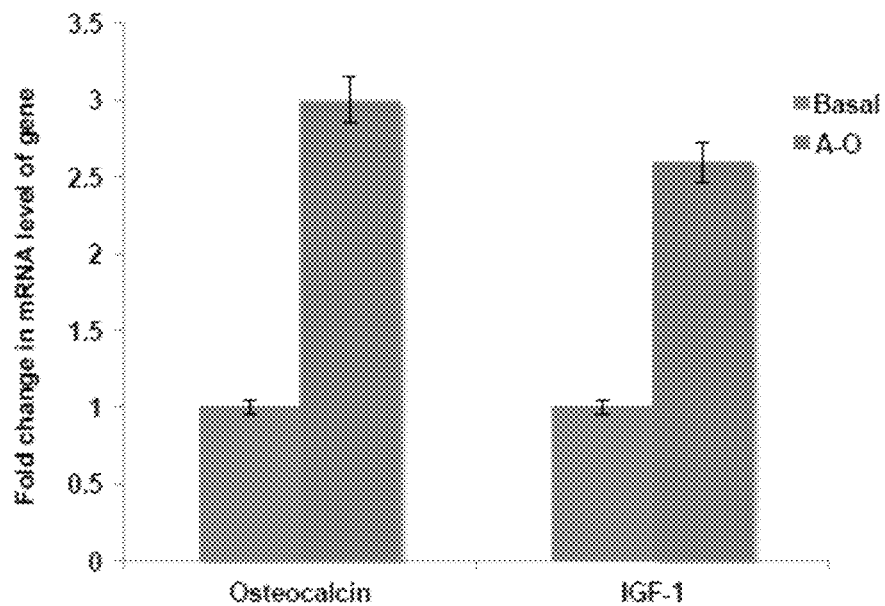

FIG. 12 demonstrates the effect of A-O complex on mRNA transcription of osteocalcin and IGF-1 in osteoblast-osteoclast cultures, in accordance with an embodiment of the present disclosure. The significance of the differences was evaluated by two-way ANOVA, followed by individual comparison using Bonferroni post test. Data are shown as mean±SEM, n=4.

Figure 13:
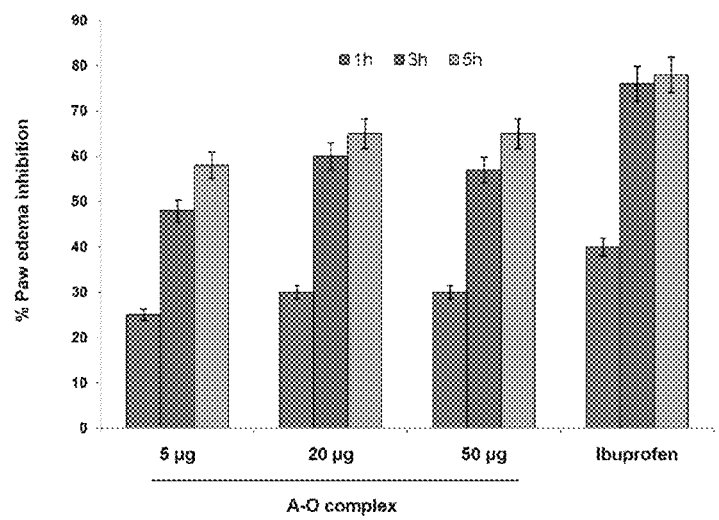

FIG. 13 is a bar diagram which demonstrates the anti-edematogenic effect of different concentrations of A-O complex against carrageenan induced paw inflammation in mice, in accordance with an embodiment of the present disclosure.

Figure 14:
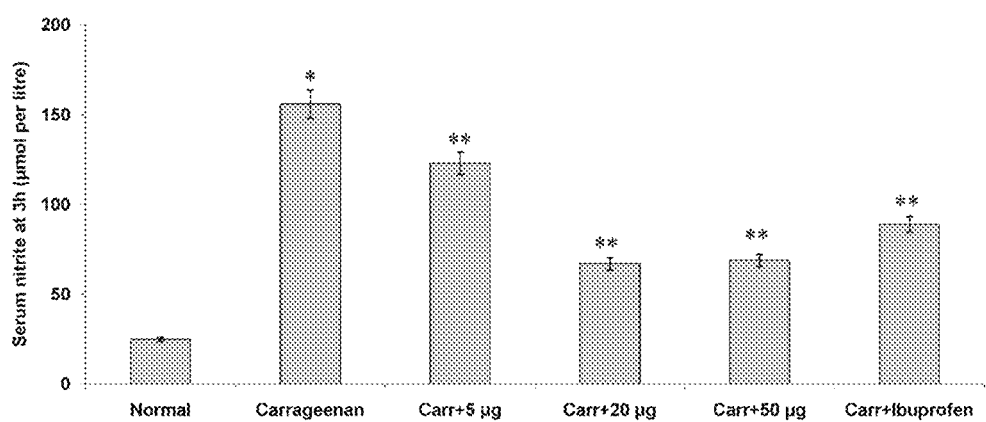

FIG. 14 demonstrates the inhibitory effect of A-O complex against carrageenan induced nitrite production in serum of mice, in accordance with an embodiment of the present disclosure. The significance of the differences was evaluated by two-way ANOVA, followed by individual comparison using Bonferroni post test. Data are shown as mean±SEM, n=4. *statistical significance with normal, **statistical significance with carrageenan control P<0.05.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term undercarboxylated osteocalcin is the form of osteocalcin without any carboxylation at glutamic acids 17, 21 and 24 of the peptide. Throughout the present disclosure, the term undercarboxylated osteocalcin or Glu-OC have been used interchangeably.

The term Abeta 1-42 or Abeta 42 is a 42 amino acid form of beta amyloid that plays a central role in Alzheimer's disease (AD). Throughout the specification the terms Abeta 1-42 or Abeta 42 have been used interchangeably.

The term ConcanavalinA or ConA is a plant multivalent lectin that has been used in the field of molecular biology and immunology because it binds to most mammalian cells and serves as a model for immunological response [Petty H R, Ware B R. Macrophage response to concanavalinA: effect of surface cross linking on the electrophoretic mobility distribution. 1979; 76: 2278-2282]. Throughout the specification the terms concanavalinA or ConA have been used interchangeably.

The term "immunomodulation" a process of resetting of the inflammatory response by modifying or regulating it. The term "immunomodulation" herein describes the down-regulation of over produced inflammatory mediators without impairing the normal immune or inflammatory response to defend against infection. It does not mean immunosuppression or anti-inflammation. Throughout the specification the term immunomodulation has been used interchangeably.

The term 'activated macrophage' denotes macrophages stimulated by cytokines (interferon gamma, granulocyte-monocyte colony stimulating factor, and tumor necrosis factor alpha), bacterial lipopolysaccharide, plant lectins like concanavalinA (ConA), extracellular matrix proteins, and other chemical mediators. Terms like activated macrophages and macrophages used herein have different meanings. Throughout the specification the term activated macrophage have been used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure provides the remedy for managing the amyloid related disorders in the form of composition comprising osteocalcin and a complex comprising Abeta 1-42 and undercarboxylated osteocalcin.

Sequence Listing

```
SEQ ID NO: 1 represents the amino acid sequence
of Abeta 1-42 peptide. Molecular weight = 4514.1
DAEFRHDSGYEVHHQKLVFFAEDVGSNKGAIIGLMVGGVVIA SEQ ID NO: 2 represents the amino acid sequence
of undercarboxylated osteocalcin (Disulfide
bridge: C23-29). Molecular weight = 5797.5
YLYQWLGAPVPYPDPLEPRREVCELNPDCDELADHIGFQEAYRRFYGPV
```

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2.

In an embodiment of the present disclosure, there is provided a peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2, wherein the undercarboxylated osteocalcin is having uncarboxylated glutamic acid residues at positions 17, 21, and 24.

In an embodiment of the present disclosure there is provided a peptide complex herein, wherein Abeta 1-42 peptide is full length mature Abeta 1-42 peptide as set forth in SEQ ID NO: 1. In another embodiment of the present disclosure, Abeta 1-42 comprises first 10 amino acids of mature Abeta 1-42 peptide as set forth in SEQ ID NO: 1.

In an embodiment of the present disclosure, there is provided a peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2, wherein the complex modulates inflammation by modulating the phenotype of activated macrophages or macrophage related cells.

In an embodiment of the present disclosure, there is provided a peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2, wherein the macrophage related cells is selected from the group consisting of peripheral blood monocyte/macrophages, microglia, dendritic cell, and osteoclasts.

In an embodiment of the present disclosure, there is provided a peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2, wherein modulating inflammation leads to modulation of diseases selected from the group consisting of macrophage activation syndrome, cardiovascular disease, atherosclerosis, systemic lupus erythematosus (SLE), inflammatory diseases of brain, Kawasaki disease, adult-onset Still's disease, immunologic disease, diabetes, and obesity.

In an embodiment of the present disclosure, there is provided a peptide complex comprising Abeta 1-42 peptide and undercarboxylated osteocalcin (Glu-OC), wherein Abeta 1-42 peptide is represented by SEQ ID NO: 1, and undercarboxylated osteocalcin is represented by SEQ ID NO: 2, and wherein the complex is used for immunomodulation.

In an embodiment of the present disclosure, there is provided a peptide complex comprising Abeta 1-42 peptide and undercarboxylated osteocalcin (Glu-OC), wherein Abeta 1-42 peptide is represented by SEQ ID NO: 1, and undercarboxylated osteocalcin is represented by SEQ ID NO: 2, wherein the complex is used for immunomodulation, and wherein the complex increases the expression of CD36 scavenger protein in macrophages related cell, thereby leading to immunomodulation.

In an embodiment of the present disclosure, there is provided a peptide complex comprising Abeta 1-42 peptide and undercarboxylated osteocalcin (Glu-OC), wherein Abeta 1-42 peptide is represented by SEQ ID NO: 1, and undercarboxylated osteocalcin is represented by SEQ ID NO: 2, wherein the complex is used for immunomodulation, wherein the complex increases the expression of major histocompatibility complex class II molecules, thereby leading to immunomodulation.

In an embodiment of the present disclosure, there is provided a composition comprising: (a) a peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2, and (b) at least one pharmaceutically acceptable excipient or carrier.

In an embodiment of the present disclosure, there is provided a peptide complex as described herein, wherein the complex is used in preparation of medicament.

In an embodiment of the present disclosure, there is provided a method of treating a subject having inflammation, said method comprising, administering to the subject a therapeutically effective amount of a peptide complex comprising Abeta 1-42 peptide and undercarboxylated osteocalcin (Glu-OC), wherein Abeta 1-42 peptide is represented by SEQ ID NO: 1, and undercarboxylated osteocalcin is represented by SEQ ID NO: 2.

In an embodiment of the present disclosure, there is provided a method of treating a subject having inflammation, said method comprising, administering to the subject a therapeutically effective amount of a composition comprising: (a) a peptide complex comprising Abeta 1-42 peptide and undercarboxylated osteocalcin (Glu-OC), wherein Abeta 1-42 peptide is represented by SEQ ID NO: 1, and undercarboxylated osteocalcin is represented by SEQ ID NO: 2, and (b) at least one pharmaceutically acceptable excipient or carrier.

In an embodiment of the present disclosure, there is provided a process for preparing a peptide complex comprising Abeta 1-42 peptide and undercarboxylated osteocalcin (Glu-OC) for modulating inflammation, said process comprising: (a) obtaining undercarboxylated osteocalcin having an amino acid sequence as set forth in SEQ ID NO: 2; (b) obtaining Abeta 1-42 peptide having an amino acid sequence as set forth in SEQ ID NO: 1, and (c) contacting the undercarboxylated osteocalcin and the Abeta 1-42 peptide under suitable conditions to obtain the peptide complex.

In an embodiment of the present disclosure, there is provided a method of identifying a compound for modulating inflammation, said method comprising: (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation. In another embodiment of the present disclosure, Abeta 1-42 peptide is represented by SEQ ID NO: 1.

In an embodiment of the present disclosure, there is provided a compound identified by a method comprising: (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation.

In an embodiment of the present disclosure, there is provided a pharmaceutical composition comprising a compound identified by a method comprising: (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation. In another embodiment of the present disclosure, the pharmaceutical composition further comprises a pharmaceutically acceptable excipient or carrier.

In an embodiment of the present disclosure, there is provided a method of identifying a compound, said method comprising: (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation, and wherein the compound is undercarboxylated osteocalcin.

In an embodiment of the present disclosure, there is provided undercarboxylated osteocalcin for use in modulation of inflammation.

In an embodiment of the present disclosure, there is provided a pharmaceutical composition comprising undercarboxylated osteocalcin for use in modulation of inflammation. In another embodiment of the present disclosure, the pharmaceutical composition further comprises a pharmaceutically acceptable excipient or carrier.

In an embodiment of the present disclosure, there is provided a method of treating a subject having inflammation, said method comprising, administering to the subject a therapeutically effective amount of a compound identified by a method comprising: (a) obtaining Abeta 1-42 peptide; (b) adding a compound to the Abeta 1-42 peptide; and (c) screening for formation of a complex between the Abeta 1-42 peptide and the compound wherein the complex leads to modulation of inflammation. In another embodiment of the present disclosure, the compound is undercarboxylated osteocalcin.

In an embodiment of the present disclosure, there is provided a method of treating a subject having inflammation, said method comprising, administering to the subject a therapeutically effective amount of a composition comprising a compound identified by a method comprising: (a) obtaining Abeta 1-42 peptide; (b) adding a compound to the Abeta 1-42 peptide; and (c) screening for formation of a complex between the Abeta 1-42 peptide and the compound, wherein the complex leads to modulation of inflammation. In another embodiment of the present disclosure, the pharmaceutical composition further comprises a pharmaceutically acceptable excipient or carrier. In yet another embodiment of the present disclosure, the compound is undercarboxylated osteocalcin.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

The subsequent paragraphs describe the claimed invention of the present disclosure by way of examples. Examples and data have been depicted using cellular models in vitro like RAW267.4 macrophage cell line and EOC20 microglia cell line and in vivo mouse models such as 5×FAD Tg mice for abnormal amyloid formation and deposition. All the studies performed using said mice are approved by the Institutional Animal Ethics Committee (IAEC/AQ/2016/150). Effect of A-O complex have been demonstrated by studying the levels of relevant biomarker genes and proteins. Further, though the effect of A-O complex is demonstrated in macrophage system, the composition is effective against wide range of disease involving other immunomodulatory cells and cells that are involved in inflammation.

List of Primers Used in the Study:

TABLE 1

| S1 No. | Name of the protein | Gene Name | Primer Assay catalogue number from Qiagen (SABiosciences) |
|---|---|---|---|
| 1. | Osteocalcin Bone gamma carboxy glutamate protein | Bglap | PPM04465F |
| 2. | MHC-II or Major Histocompatibility complex | Cd74 | PPM06004F |
| 3. | CD36 | Cd36 | PPM03796D |
| 4. | LRP1 or Low-density lipoprotein receptor-related protein 1 | Lrp1 | PPM05653F |
| 5. | ApoE or Apolipoprotein E | Apoe | PPM04128B |
| 6. | Beta-actin | Actb | PPH00037G |
| 7. | Tumour necrosis factor-alpha | Tnfa | PPM03113F |

Effect of carboxylated osteocalcin (Glu-OC) against Alzheimer Disease pathology was tested in B6SJL-Tg [(APPSwFlLon,PSEN1*M146L*L286V) 6799Vas/Mmjax] also known was the 5×FAD Tg mice. This mouse model (Jackson Laboratory, Bar Harbour, Me.) represents aggressive amyloid deposit.

Two month old 5×FAD Tg mice, both male as well as female were used for the study. For the purposes of this study wild type mice is referred to as Wt and 5×FAD mice is referred to as Tg. For experimentation, the mice were divided in below groups for treatment:
1. Wild type mice given vehicle (1×PBS or phosphate buffered saline; pH 7.4).
2. 5×FAD Transgenic mice given vehicle.
3. 5×FAD Transgenic mice given undercarboxylated osteocalcin (Glu-OC) subcutaneously at dose of 300 ng per mouse of weight ranging from 25-28 g for 2 months.

Development of A-O complex: For the purposes of the present study, recombinant Abeta1-42 was procured from r-peptide and Glu-OC was purchased from Anaspec Inc. However, the complex as disclosed herein, can also be prepared by generating the protein, in-house, using recombinant DNA technology.

Preparation of Glu-OC: 0.25 mg of osteocalcin was dissolved in 0.1% $NH_4OH$, at a concentration of 1 µg/µl.

Glu-OC at a dose of 300 ng per mouse was administered subcutaneously for 2 months. To evaluate the potential of Glu-OC against development of Alzheimer's disease in 5×FAD Tg mice (a mouse model for Alzheimer's disease), the following methodologies used conducted: Morris water maze (MWM) test, immunohistochemistry, double immunostaining, ELISA and Congo Red staining. For MWM test, a navigation task that was performed to measure spatial memory, movement control and cognitive mapping, a tank with the diameter of 120 cm filled with the water having the temperature around 26° C. was divided into the four quadrants wherein one of the quadrants contained a transparent platform immersed such that the level of the water is about 1 cm above the surface of the platform. This platform is called the "hidden platform" since is it invisible to the mouse. On the first day of the training, the mouse is kept on the platform for the 15-20 seconds and then dropped in the opposite quadrant of the platform containing quadrant in the tank. The animal is allowed to search for the hidden platform and guided to the platform, if the animal is unable to find it in 120 seconds. The training was given for the five consecutive days, with the video recording and the track of the animal was also recorded using the Any-maze animal behaviour software. Time taken to find the hidden platform is calculated and plotted.

For immunohistochemistry, sacrificed animals were perfused using 4% paraformaldehyde perfusion through the heart and the brains were harvested and submerged in the same fixative for not more than 24 hours. Brains were then washed in 1×PBS (pH 7.4) and placed in 30% sucrose-PBS solution where these initially floated owing to the weight of the sucrose. Upon saturation, the brains sank to the bottom of the sucrose solution. These were then removed and washed in PBS. Brain samples were quick frozen in liquid nitrogen and then embedded in polyfreeze tissue freezing medium in a plastic mould inside a cryostat where in temperature was −20° C. The samples were then stored in −80° C. until sectioning. Sections of 15-20 micrometre was cut in a cryostat and laid over high adsorbent microslides. For unmasking antigens, slides were heated at 55° C. for 10 min followed by hydration in PBS for 5 min and then permeabilization using 0.1% Triton X-100 in PBS containing 1% BSA and 1% normal goat serum (IHC buffer). For immunostaining, brain sections were incubated in primary antibodies (fibrillar Amyloid beta antibody, catalogue number MABN638 was from Millipore-Merk; osteocalcin antibody-catalogue number sc365797 was from Santa Cruz Biotechnology; Abeta1-42 antibody D923A #14974 was from Cell Signaling Technology) diluted in IHC buffer in a humidified chamber at room temperature overnight. For double immunostaining, specific antibodies against Abets42 and osteocalcin were incubated together with brain sections. After rinsing with PBS three times for 5 min each, sections were incubated with the appropriate secondary antibody conjugated with AlexaFluor 594 or 488 (Molecular Probes, Invitrogen) for 2 h at room temperature. After rinsing with PBS, the coverslips were mounted with ProLong anti-fade mounting medium containing 4',6-diamidino-2-phenylindole (DAPI) and imaged. Congo Red staining was done using staining kit from Abcam (ab150663) according to manufacturer's instructions.

ELISA or enzyme linked immunosorbent assay was conducted on soluble and insoluble fractions prepared from brain samples. (a.) Preparation of soluble or DEA fraction or non-plaque associated Abeta. Brain homogenate at a concentration of 100 mg brain tissue per ml extraction reagent was prepared using 0.2% diaethylamine or DEA and centrigued at 100,000 g in an ultracentrifuge for 1 hour at 4° C. (54,000 rpm in ~100.3 rotor). The supernatant (soluble fraction) was neutralized by addition of ⅒th volume of 0.5M Tris-HCl; pH 6.8 and vortexed gently. For preparation of insoluble fraction or FA (ormic acid) fraction or plaque associated Abeta, 10% brain homogenate prepared using RIPA buffer containing protease-phosphatase cocktail (Sigma-Aldrich, St Louis, Mo., USA) was mixed with cold formic acid. To 200 microlitre homogenate, 440 microlitre of formic acid was added and mixed in a microcentrifuge tube and sonicated for 1 min on ice. The probe was moved up and down in between intervals. The homogenate was spun at 135,000 g for 1 hour which is approx 50,000 rpm for 100.3 rotor. Further 210 microlitre of supernatant was neutrilized using FA neutrilization buffer [1M Tris base, 0.5M $Na_2HPO_4$, 0.05% $NaN_3$=60.57 g Tris base, 35.5 g $Na_2HPO_4$, 2.5 ml 10% $NaN_3$ and diluted to 500 ml and stored at room temperature since lower temperature will facilitate precipitation], flash frozen. Prior to performing ELISA, samples were incubated for 5 min at 37° C. to clarify the solution and solubilize the precipitate. Protein estimation of brain homogenates were performed using Pierce BCA protein assay kit according to the manufacturer's instructions. In some samples, proteins from homogenate was precipitated using 10% ice cold trichloroacetic acid (TCA) which was spun and re-dissolved in 0.1 N NaOH. The protein estimation of these samples were then conducted using Pierce BCA protein assay kit. To quantify the protein by ELISA, samples were applied on to high adsorbent 96-well flat bottom microtiter plates alongside recombinant standards at a concentration ranging from 0.001-0.1 ng and incubated for 2 h at 37° C. The unbound material was washed with phosphate buffered saline (pH 7.4) containing 0.2% Tween 20 (PBST), blocked with 10% BSA in PBST for 1 h at 37° C. After washing with PBST, 100 µl of primary antibodies at recommended dilutions was added per well and incubated for 3 h at 37° C. After washing with PBST, the wells were added with streptavidin horseradish peroxidise conjugated antibody (0.5 µg/ml) for 1 h and then treated with 3,30,5,50 tetramethyl-benzidine (TMB) ready to use liquid substrate. Reaction was stopped using 100 µl of 1M HCl and the OD of each well was measured at 450 nm and 550 nm in an ELISA reader. 450 nm reading were subtracted from 550 nm values to correct imperfections in the microplate (Tecan microplate reader Infinite 200 PRO series, Switzerland with Magellan™ software). A curve fitting statistical software was used to plot a four-parameter logistic curve to calculate the results.

Results: 5×FAD mice treated with Glu-OC showed significant reduction in amyloid pathology in brain (FIG. 1C). Although reduction in amyloid plaques was evident, the morphology of the reduced plaques suggested presence of fibrillar aggregates as evidenced by Congo Red stain (ordinary light) (FIG. 1Cb-d). This observation was cross verified by immunostaining using a fibrillar specific antibody for Abeta42. The result was positive for intense fibrillar Abeta42 structures that were concentrated to specific areas of the brain cortex (FIG. 1D). In conjunction, it was also observed that treatment with Glu-OC reduced only insoluble or plaque associated Abeta42 and increased the soluble Abeta42 level in brain (FIG. 1E) even though cognitive function was restored as evidenced by reduced escape latency as compared to 5×FAD Tg control mice that showed higher latency time to find the platform (FIGS. 1A and 1B).

Next, whether Glu-OC promoted fibrillization of Abeta42 was investigated in situ. For this study, different concentrations of Glu-OC viz. 10 ng, 5 ng and 3 ng were incubated with a fixed concentration of Abeta42 (100 micromolar) and visualized using transmission electron microscopy (TEM). For that Abeta42 control and mixtures containing Abeta42 and Glu-OC were diluted 100 folds in ultrapure water and applied on to electron microscope carbon coated grids. After keeping the samples for 5 minutes, the excess was washed off with ultrapure water and surplus sample and water were wicked away using absorbent paper. The samples were negatively stained using 1% uranyl acetate stain, dried and analyzed in a transmission electron microscope CM10 Philips operated at 80 kV. To determine the biophysics of Abeta42 aggregation in the presence of Glu-OC, Thioflavin T (ThT) binding assay assay was performed. ThT assay measures the changes in fluorescence intensity of ThT upon binding to amyloid fibrils. For assay, 1 ml filtered solution of 50 µM aqueous solution of Thioflavin T (in glycine-NaOH buffer, pH 8.0) was contacted with 2 µl of 100 µM Abeta42 sample solution in the presence or absence of Glu-OC and incubated for 15 min at 25° C. in the dark. The resulting ThT fluorescence intensities of samples were measured at an emission wavelength of 480 nm and excitation wavelength of 440 nm and 5 nm slit width using a Jobin Vyon Horiba Fluoromax-4 spectrofluorimeter. The inner filter effect was taken into account using the Equation: Fc=F×anti log[(Aex+Aem)/2] where Fc is the corrected flourescence and F is apparent fluorescence, Aex and Aem are the absorbances of the samples at excitation and emission wavelengths respectively.

Results: While Abeta42 at 100 micromolar concentration formed immature and cross-linked amyloid structures (FIG. 2A), Abeta42 samples treated with Glu-OC demonstrated fibrillization (FIG. 2B-2D). Mature fibrils were observed when Abeta42 was incubated with 3 ng of osteocalcin (FIG. 2E-2F). The same Abeta42+Glu-OC (3 ng) mixture was performed Thioflavin or ThT assay alongside Abeta42 control and high enhancement of fluorescence emission of ThT was seen in this mixture as compared to Abeta42 control suggesting the advancement of fibrillization Abeta42+Glu-OC (3 ng) mixture as early as $8^{th}$ hours post initiation of experiment when compared to Abeta42 control (FIG. 2G).

Since Glu-OC promoted fibrillization, the next objective was to assess whether Glu-OC co-localized with Abeta42 in vivo. For this, brain sections Glu-OC treated Tg mice were double immunostained with Abeta42 and osteocalcin antibodies.

Results: Both Abeta42 and osteocalcin co-localized when the concentration of osteocalcin and Abeta42 was above physiological amounts (FIG. 3).

Predicted structure of A-O complex—Bioinformatics study: The three-dimensional structure of Abeta1-42 peptide was downloaded from PDB with the PDB id: 1IYT, which contained the solution structure of Abeta (1-42) monomer. Experimentally resolved three-dimensional structure of human osteocalcin was modelled computationally (FIG. 4A). The sequence of human osteocalcin was retrieved from UniProtKB with accession number P02818 (OSTCN_HUMAN), in which the region 52 to 100 amino acids corresponds to the osteocalcin peptide. The signal peptide (from 1 to 23 aa) and the propeptide (from 24 to 51 aa) were not considered for the study. Protein BLAST was performed against the PDB database to select the suitable template for structure prediction. Crystal structure of porcine osteocalcin with PDB id 1Q8H was selected as the template for the study. As the homology modelling method resulted in truncated structure only, Ab initio modelling was carried out to obtain the entire length (49 amino acids) of under-carboxylated fragment of osteocalcin. The sequence of osteocalcin was submitted to the online I-TASSER (Iterative Threading ASSEmbly Refinement) server for structure prediction. I-TASSER server (Zhang Y. I-TASSER server for protein 3D structure prediction. BMC Bioinformatics. 2008; 9: 40.) uses a combined multiple threading and ab initio approach with full-length atomic model construction by iterative template fragment assembly simulations. The server was ranked first in several CASP (Critical Assessment of protein Structure Prediction) experiments. The top predicted model from I-TASSER was downloaded and the C-score (confidence score) was noted. The structure was then analyzed for its stereo-chemical quality and stability using Ramachandran Plot in PROCHECK program and ERRAT2. Molecular docking between undercarboxylated osteocalcin and Abeta1-42: The monomeric structure of amyloid abeta1-42 and the ab initio predicted structure of osteocalcin were employed for the docking study. Both the 3D structures were submitted to the online docking servers PATCHDOCK and ZDOCK. Patchdock server uses a geometry based molecular docking algorithm to find near-native conformations with good molecular shape-complementarity. The initial docked solutions after the rigid-body protein-protein docking from Patchdock were refined and re-ranked based on the global energy (binding energy) using FIREDOCK program. The refined complexes were further closely analyzed for the key interacting residues and the favorable interactions like hydrogen bonds. The docked complexes from ZDOCK were downloaded and analyzed for their binding poses and interacting residues. PRODIGY server was employed to compute the binding affinity ($\Delta G$) expressed in kcal mol$^{-1}$ and the dissociation constant ($K_d$) at a given temperature (25° C. by default) for the top docked poses. PRODIGY (PROtein binDIng enerGY prediction) is a web server that predicts the binding strength for a given protein-protein complex based on intermolecular contacts and properties derived from non-interface surface. The list of contacting residues at the protein-protein interface was also obtained from the server.

Results: The sequence of human osteocalcin, retrieved from UniProtKB with accession number P02818 is a 49 amino acid long polypeptide chain. The template structure of Porcine Osteocalcin (PDB id 1Q8H) bear 85% sequence identity with human osteocalcin in sequence similarity search using BLAST P tool. Homology modeling resulted with a sequence length of 34 amino acids only. Therefore ab-initioprediction method was carried out using I-TASSER server. C score (Confidence score) for the best model was found to be −0.88, which is an accepted value as it lies between [−5,2]. Higher the C score, higher the quality of the model. The predicted TM score, which is a measure of structural similarity between the two proteins, i.e. the template and the model was found to be 0.6+−0.14 which is acceptable as it is higher than 0.5 (means both proteins take up the same fold in SCOP/CATH). The 3D model for osteocalcin is shown below. It is undercarboxylated at the residues 68,72,75 (here in the chain of 49 length, the sites are at 17, 21 and 24) and retains the disulfide bridge between 74 to 80 (i.e. here between C23 and C29). The stereochemical quality of the modelled structure was found to be satisfactory when verified using PROCHECK AND ERRAT2 servers. 70.3% of the amino acids were found to be in core region of the Ramachandran Plot, 24.3% in the allowed region, 5.4% in the generously allowed region and 0.0% was found to be in the disallowed regions. This shows that the model is stable and properly folded with residues taking up appropriate phi-psi values. ERRAT2 program gave an overall quality factor of 95.122 which show the model is of good quality comparable to a good high-resolution structure. Both the docking servers provided comparable docked poses for the peptide-peptide interaction under study. The best docked poses (top 10) from patchdock and top 10 poses from Zdock (representative images as FIGS. 10C and 10D) were downloaded and further analyzed for the key interacting residues. The following amino acids in Osteocalcin peptide were found to interact more frequently with residues of amyloid beta42 peptide. Tyr1, Tyr3, Gln4, Trp5, Leu6, Pro9, Val10, Tyr12, Pro13, Pro15, Leu16, Glu17, Glu21, Glu24, Glu31 and Arg44 (FIG. 4C). Top poses from both the servers were further studied for their predicted $K_d$ and $\Delta G$ values. Best complex from ZDOCK server was found to have $\Delta G$ value of −6.4 Kcal mol$^{-1}$ and $K_d$ 2.0e$^{-05}$ M and the best complex from Patchdock server was found to have $\Delta G$ and $K_d$ of −5.2 Kcal mol$^{-1}$ and 1.5e$^{-04}$ respectively.

Interactions of the residues Glu17, Glu21 and Glu24: After the docking study, the best docked poses (top 10 from patchdock server and top 10 from Zdock server) were analyzed for the key interactions. The amino acids Glu17, Glu21 and Glu24 were among the critical residues of Osteocalcin peptide. Glu21 was found to have a strong electrostatic interaction (attractive charge) with Arg5 of Amyloid beta42 peptide within a distance of 5.03 A° in one docked pose whereas in an alternate docked pose Glu17 was found to have a similar but stronger electrostatic interaction (attractive charge) with Arg5 of Amyloid beta42 peptide within a distance of 3.78 A°. Glu24 was found to form a conventional hydrogen bond within a distance of 2.68 A° with the residue Ser8 of Amyloid beta42 peptide. Glu21 and Glu24 were seen more frequently interacting with Amyloid beta42 peptide when compared to Glu17. Representative images are represented by FIGS. 4D and 4E and the interactions have been summarized in the Table below:

TABLE 2

| Interaction | Type of Interaction | Distance (A°) |
|---|---|---|
| ARG5:NH2 - GLU21:OE2 | Electrostatic (attractive charge) | 5.03 |
| ARG5:NH1 - GLU17:OE2 | Electrostatic (attractive charge) | 3.78 |
| SER8:OG - GLU24:OE1 | Conventional hydrogen bond | 2.68 |

The results so far suggested that a complex of Glu-OC and Abeta42 is plausible; but is the complex a promising therapeutic? At what ratio can Abeta42 and Glu-OC form a complex with pharmacological property? These were queries that were addressed next. A series of different concentrations of Glu-OC (25 ng to 0.1 ng) were incubated with Abeta42 (100 micromolar concentration) for 4 hours and the effect of these mixtures were evaluated in ConA stimulated macrophage system. For this murine RAW264.7 (macrophage) cells were employed. The cells were maintained in RPMI 1640 media supplented with glutamine (2 mM) and FBS (10%). No trypsination was performed and subculture was done using a cell scraper after cultures reached 65-70% confluency. For experimentation, mixtures of Abeta42 and Glu-OC were pre-incubated with 2×10⁶ cells for 30 mins after which ConA was added into cultures and the level of TNF-alpha was analyzed in cell culture supernatant by ELISA using anti-TNF alpha antibody from Abcam (ab6671).

Results: % Inhibition profile showed that doses 0.1 to 5 ng of Glu-OC with Abeta42 showed inhibitory effect against ConA induced TNF-alpha production in macrophage cultures.

Further the same mixtures were evaluated for A11 immunoreactivity by ELISA and Western blot. This was performed using oligomer A11 polyclonal antibody from Invitrogen, Thermo Fischer. For ELISA 0.5 microgram per ml of Abeta42 controls and mixtures of Abeta42 and Glu-OC were loaded on to high adsorbent ELISA plates and the procedures were the same as mentioned above. For Western blot 1 microgram per ml concentration of Abeta42 controls and mixtures of Abeta42 and Glu-OC were run on Tricine gel (Bio-Rad) at 80 V and transferred onto nitrocellulose membrane (0.2 micrometre) and allowed to dry. The membrane was blocked with 5% BSA in 0.1% Tween20 and then incubated with A11 antibody for 1 hour followed by three rounds of washing in Tris buffered saline containing 0.1% Tween20 (TBST) with 5 min interval each. Thereafter the membrane was incubated in anti-rabbit HRP conjugated secondary antibody for 1 hour followed by TBST washes (thrice) and imaged using chemiluminescence reagent in an imager and imaged using ImageQuant™ LAS4000 software.

Results: Mixtures of Abeta42 with 0.1 to 5 ng Glu-OC were less reactive with A11 as evidenced by ELISA (FIG. 6A). Tricine gel separation of mixtures followed by immunostaining with A11 antibody showed that Abeta+Glu-OC (3 ng) did not produce any A11 reactive oligomers (FIG. 6A). Mixtures containing 10 and 5 ng of osteocalcin showed reactive bands between 30 and 300 kDa.

Effect of Abeta-Glu-OC (3 ng) mixture on macrophage integrity: To determine whether the mixture produced any toxicity lactate dehydrogenase (LDH) assay was performed. Briefly, the cells were incubated with the mixture under serum starved conditions for 1 hour followed by LDH assay. LDH was assayed using In vitro toxicology assay kit from Sigma-Aldrich, St. Louis, Mo., USA (cat. no.-TOX7) as per the manufacturer's directions. LDH assay substrate solution, LDH assay dye solution and 1×LDH assay cofactor were provided with the kit. Briefly, cell culture supernatants were spun at 250 g for 4 min to pellet remaining cells. To this LDH assay mixture was added and incubated at room temperature in the dark for 20-30 min. The reaction was terminated by the addition of ¹⁄₁₀ volume of 1N HCl. Absorption was taken 490 nm with the help of in a Tecan Microplate reader, Switzerland with Magellan™ software.

Results: Macrophages treated with the mixture did not show any rise in intracellular LDH with respect to control (FIG. 6B). The cell culture supernatants of Anets42+Gla-OC (3 ng) treated cells did not show rise in LDH. Conversely, Abeta42 control showed high intracellular level of LDH without any LDH release to supernatants. Positive control $H_2O_2$ (hydrogen peroxide) showed rise in intracellular LDH and also induces LDH release to cell culture supernatants.

Visualization of Abeta42+Glu-OC (3 ng) mixture—the A-O complex: The mixtures were visualized by atomic force microscopy or AFM. For that the samples were diluted 50 folds with ultrapure water. 5 microlitre of the diluted sample was immediately deposited onto the freshly cleaved mica surface and left for two minutes. After that each sample was rinsed with ultrapure water and dried under the nitrogen flow. Samples were imaged in air in non-contact acoustic AC mode using the Atomic force microscope 5500. AC cantilever (normal spring constant of cantilever) was used. The topographic imaged of all the samples were used for the analysis using the SPIP software.

Results: AFM showed that A-O complex contained predominantly two structures—hydrated structures of height 3-5 nm and immature fibrillar structures of 1-2 nm height (FIG. 6F).

Scheme 1 details the steps in the preparation of the A-O complex.

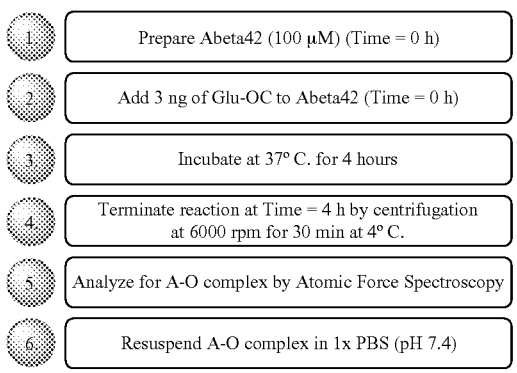

Preparation of Abeta1-42 peptide solution and exposure to Glu-OC: 1 mg of Abeta1-42 peptide was resuspended in 1% $NH_4OH$, at a concentration of 1 mg/ml. This was sonicated for 30 seconds to 1 minute after it has gone into solution. 100 of Abeta1-42 solution was aliquoted to 10 silicone free eppendorf tubes and lyophillized. For aggregation reaction, 100 μl of 1× Dulbecco PBS (pH 7.4) was added to each tube. This was quickly divided into two 50 g aliquots. One served as control whilst the others were immediately exposed to Glu-OC. A-O complex, as employed in the present study, was prepared as stepwise as described below:

a) 100 μM of Abeta1-42 was prepared.
b) 3 ng of Glu-OC was added to the Abeta1-42
c) The mixture of Abeta 1-42 and Glu-OC was incubated at 37° C. undisturbed for 4 hours.
d) The reaction was terminated (Time=4 h) by centrifuging the mixture of Abeta 1-42 and Glu-OC at 6000 rpm for 30 minutes at 4° C.
e) Post 4 hours A-O complex was visualized by Atomic force microscopy (AFM).

To determine the immunomodulatory effect of A-O complex, serum starved macrophages were exposed to the complex. Macrophages (1×10⁶ cells) were serum starved for 30 min after which cells were exposed to A-O complex. After 1 hour, cells were washed with 1×PBS (pH 7.4) and harvested using cell dissociation solution. Then the cells were suspended in ice cold staining buffer (100 μl) and centrifuged at 1000 rpm for 5 min at 4° C. The cells were resuspended in 100 μl ice cold staining buffer for 10 min at 2-8° C. and pellet resuspended in 50 μl staining media. To this 2 μl of Fc block or anti-mouse CD16/CD32 was added for 10 mins and washed with staining buffer. The cells were resuspended in 50 μl of staining buffer and incubated with fluorescent-tagged CD36 antibody (e-biosciences) for 25-30 min on ice. The excess stain was removed by washing and pelleting down using staining buffer thrice by spinning and removal of staining buffer. The cell suspension was fixed 1:1 ratio (staining buffer:fixative) and analysed within 48 h in ARIA3 DIVA software version 6.1. Further, expression of MHC-II, and CD-36, was also determined in the microglial cells via qPCR. For this RNA extraction was performed using RNA extraction kit from Qiagen according to the manufacturer's instruction. cDNA synthesis was performed using cDNA synthesis kit from Qiagen. To perform qPCR, 10 ng cDNA (per well) was amplified using the Light Cycler 480 Sybergreen I Master reagent (Roche Diagnostics, Indianapolis, Ind.) and primers (commercially purchased from SABiosciences, Qiagen) in the Light Cycler 480 (Roche Diagnostics, Switzerland) under following cycling conditions: 3 min at 95° C., 15 sec at 95° C., 20 sec at 60° C., 25 sec at 72° C. for 40 cycles. Following amplification, fold changes in gene expression versus β-actin (reference) analysis was determined using the $2^{\Delta\Delta CT}$(Livak) method. The primers used are shown in Table 1.

For uptake assays, AlexaFluor488 tagged Tottori-Japanese mutation containing Abeta42 and DiI-labelled oxidized LDL (1,1'-dioctadecyl-3,3,3',3'-tetramethylindocarbocyanine perchlorate, 1 microgram per ml; Intracel) were employed. For labelling of mutated Abeta42, Alexa Fluor488 TFP ester Microscale Labeling Kit (A30006, Invitrogen) according to manufacturer's instructions. Briefly, 50 µl of 100 µM Abeta was pH adjusted to pH 9 with 5 microlitre of 1 M $NaHCO_3$, followed by addition of 4 microlitre of the $H_2O$ solubilized reactive dye. Incubation at room temperature (~22° C.) was performed for 15 min followed by immediate addition of 55 microlitre of the labeling reaction mixture onto a spin column packed with a 425 microlitre slurry of Biogel P-6 resin for removal of unincorporated dye. The resulting eluent (pH 7.4) was stored for up to 2 days at 4° C. or used immediately for cellular uptake experiments. Both ligands were exposed after pre-treatment of cells with A-O complex for half an hour. The ligands were exposed to cell cultures for 1 hour after which cells were either quenched with trypan blue (0.2%) or given acid wash. Cells were detached using cell dissociation solution and the fluorescence was measured at 514 nm excitation/550 nm emission for DiI-labelled oxidized LDL and 503 nm excitation/528 nm emission for Hilyte Abeta42 on ARIA3 DIVA software version 6.1.

Results: FIG. 7A is a bar diagram that shows changes in the mRNA level of genes studied like Cd74 (MHC-II), Cd36, Lrp1 and Apoe by qPCR. Glu-OC and Abeta42 do not elicit induction of Cd74 and Cd36 whilst A-O complex induced these two genes as evidenced by 3 fold and 8 fold increase in the mRNA levels of Cd74 and Cd36 respectively. FIG. 7B depicts the FACS results showing the increased cell surface protein expression of phagocytic CD36 receptor in the cells treated with A-O complex. Since A-O complex activated CD36, a scavenger receptor (as observed in earlier experiments), the efficacy of A-O complex to stimulate uptake of CD36 ligands such as mutant Abeta42 (mutant Aβ) and oxidized-lipoprotein (oxLDL) were tested in macrophages. It can be appreciated from the results depicted in FIG. 7C that pre-treatment of macrophages with A-O complex, facilitates the uptake of mutant Aβ and oxLDL (FIG. 7C).

To determine the immunomodulatory effect of A-O complex on activated macrophages, macrophages were activated with Concanavalin-A (Con-A), for 30 minutes and the changes in mRNA levels of Cd36, Lrp1, Cd11b, Cd74 and Apoe were analyzed by qPCR.

It was found that ConA significantly increased mRNA levels of Cd11b and Cd74 (FIG. 7D). A-O treatment significantly reversed the mRNA level of these genes to normalcy. A-O complex also significantly induced the mRNA level of Cd36 in activated macrophage cultures.

To determine the anti-inflammatory potential of A-O complex, protein level of iNOS (inducible nitric oxide synthase) in cell lysates and nitrite level in cell culture supernatants were evaluated by Western blot and Griess assay respectively. iNOS antibody used was #2982 from Cell Signaling Technology. For determination of nitrite cell culture media and Griess reagent (5% phosphoric acid containing 0.1% NEDD, 1% sulfanilamide) were mixed and incubated in dark for 10 min at room temperature. The absorbance of the violet colored product and blank (cell culture media) was measured at 540 nm. The concentration of nitrite in the sample was determined from a sodium nitrite ($NaNO_2$) standard curve.

Results: FIG. 8A, depicts the change in the expression levels of iNOS protein. As can be observed, treatment with ConA induces iNOS expression in macrophages. However, addition of A-O complex reduces the iNOS expression. Further, reduction in the ConA induced nitrite levels, was also observed in macrophage cultures upon treatment with A-O complex (FIG. 8B).

To determine the immunomodulatory effect of A-O complex in microglia, EOC20 microglial cells from ATCC (CRL-2469) was employed. The cells were cultured in high glucose Dulbecco's Minimal Essential Media (DMEM) containing 4 mM L-glutamine, 10% fetal bovine serum (FBS) and 20% LADMAC conditioned media. LADMAC media was prepared by growing 80% confluent LADMAC cell line from ATCC (CRL-2420) in alpha-minimal essential media supplemented with 10% FBS for 5 days. The spent supernatant was centrifuged at 1000 rpm for 10 min and the supernatant was filtered as used as LADMAC media. To determine the morphological changes in microglia upon exposure to A-O complex, F-actin confocal microscopy was performed. For that poly-L-lysine coated coverslips were placed in the 24 well culture dishes containing 1 ml of complete media and cells were seeded over the cover slips. Upon attaining cell confluence of 60-70%, cells were serum starved for 30 mins and then A-O complex, Abeta42 and ConA were added in separate plates for 1 hour. Post treatment, the cell culture media was then removed and cells were washed thrice with 1×PBS (pH 7.4). Cells were fixed in 4% PFA for 10 min at room temperature and then washed thrice with 1×PBS (pH 7.4). Cells were then exposed to Phalloidin-actin (F-actin) antibody for 20 min in the dark. Thereafter, cells were washed twice with 1×PBS (pH7.4) and mounted using DAPI Fluormount (Invitrogen, Carlsbad, Calif., USA). Cells were imaged on a Zeiss LSM510 META laser-scanning confocal microscope. A PlanApochromat 63/1.4 oil-immersion DIC M27 objective (Zeiss) was used for image acquisition. [Concentration of Phalloidin-actin antibody: 300 U of Phalloidin-actin (Invitrogen, Carlsbad, USA) was dissolved in 1.5 ml methanol to yield a concentration of 200 U/ml or 6.6 µM. 1 U of phalloidin is equal to 5 µl of methanolic stock].

Results: FIG. 9A shows appearance of a microglial cell under unstimulated conditions. Upon Abeta42 addition, cells majorly showed rounded morphology with few projections (FIG. 9). ConA stimulated microglia also showed similar morphology as Abeta42 treated microglia except that the numbers of projections were higher. A-O treated microglia also showed rounded morphology with projections indicative of activation (FIG. 9D).

Next, immunomodulatory effect of A-O complex on activated microglial cells was determined. Cells were exposed to A-O complex for 1 hour post stimulation with ConA for 30 mins. Experiments were performed under serum starved conditions. The immunomodulatory effect was assessed via F-actin staining and qPCR.

Results: As can be seen in FIG. 11A, ConA stimulated cells show rounded morphology with processes indicative of activation whilst ConA+A-O treated cells show presence of cells with ramified process. The qPCR experiments suggested that A-O complex normalized CoA induced induction in Cd11b and Tnfa mRNA levels whilst it induced the mRNA level of Cd36 (FIG. 10).

Effect of A-O complex on bone cells: To determine whether A-O complex modulated bone cells, A-O complex was added to a co-culture system of osteoblast and osteoclast. MC3T3-E1 sub-clone 4 (pre-osteoblast cell line derived from new born mouse calvaria purchased from American Type Culture Collection) were cultured in α-MEM (Invitrogen, USA) supplemented with 10% fetal bovine serum and 1% anti-anti (Invitrogen, USA). Osteoblasts within the $4^{th}$ and $10^{th}$ passages were used for this study. For cell culture experiments $2 \times 10^6$ cells were seeded in 60 mm Petri plates. To initiate differentiation, cells were treated with 10 mM β-glycerophosphate and 50 µg/ml ascorbic acid. Murine RAW264.7 (macrophage) cells were used for generating osteoclasts. The cells were maintained in RPMI 1640 media supplemented with glutamine (2 mM) and FBS (10%). No trypsination was performed and subculture was done using a cell scraper after cultures reached 65-70% confluency. For generation of osteoclasts from RAW264.7 cells, cells of density 12000 cells per $cm^2$ were stimulated with 25 ng per ml of RANKL (directly with seeding) for 72-96 hours after which large multinucleated cells are seen and confirmed using TRAP5b assay. For co-culture, osteoblasts were added to developed osteoclast cells and then exposed to osteoblast differentiating media containing 10 mM β-glycerophosphate and 50 µg/ml ascorbic acid for 3 days. Thereafter the co-culture was exposed to A-O complex and the mRNA levels of osteocalcin and IGF-1 were analyzed by Real Time PCR.

Result: As depicted in FIG. 12, after 24 hours of incubation, the co-culture system treated with A-O complex displays significantly higher mRNA transcripts of osteocalcin and IGF-1 when compared to the basal levels.

Effect of A-O Complex Against Carrageenan Induced Paw Inflammation in Mice

The effect of A-O complex was tested under in vivo conditions. Carrageenan, an inflammation inducing agent was injected into the hind foot pad of mouse to induce acute inflammation. The edema attains peak at around 3 hours post carrageenan challenge. This is a convenient model to assess the anti-inflammatory potency of test drugs to reduce or prevent the development of swelling. The protocol followed herein is as per Morris (2003) [Morris C J, 2003, Carrageenan induced paw edema in rat and mouse. In: Winyard P. G., Willoughby D. A. (eds) Inflammation Protocols. Methods in Molecular Biology, Vol 225. Humana Press. Pp 115-121].

Acute inflammation induced by carrageenan is non-immune and highly reproducible. Cardinal signs of inflammation like edema, hyperalgesia and erythema build up immediately following intraplantar injection causing release of pro-inflammatory agents such as bradykinin, histamine, tachykinins, complement and reactive oxygen and nitrogen species. Neutrophils migrate to sites of inflammation and generate many pro-inflammatory reactive oxygen species. The inflammatory response is measured by increase in paw size (edema) which is maximal around 5 h post carrageenan injection and that can be modulated by specific inhibitors of inflammation [Winter, C. A., Risley, E. A., and Nuss, G. W. (1962) Carrageenan-induced edema in hind paw of the rat as an assay for anti-inflammatory drugs. Proc. Soc. Exp. Biol. 111, 544-547].

Preparation of carrageenan: To prepare 0.5% of carrageenan solution, 50 mg of lamda-carrageenan (100 mg/kg, Sigma Chemical Co., St. Louis, Mo., USA) was slowly added onto a small beaker containing 10 ml of normal saline. The powder was allowed to swell for some time and then slightly heated (not boiled) to dissolve the carrageenan. The solution was stirred during the heating. Once dissolved, the solution was cooled and aliquoted and stored at 4 degree Celsius.

Method: For experiment, the mice were acclimatized in cages under standard light and temperature settings with access to food and water ad libitum. Mice were acclimatized for 1 week in respective cages to minimize stress. At the day of experiment, mice were placed in a temporary animal restraint and 50 microlitre of carrageenan solution was administered by intraplantar injection to the right hind paw of each mouse. The left paw served as control and was administered 50 microlitre of normal saline.

To determine the efficacy of A-O complex different concentrations of complex viz. 5, 20 and 50 microgram per 100 g body weight of mice were administered intraperitoneally 1 hour before carrageenan challenge. Ibuprofen (100 mg/kg, Sigma Chemical Co., St. Louis, Mo., USA) served as positive control for the experiment. Paw size was measured by wrapping a piece of cotton thread round the paw of each rat and recording the length of the thread, the paw circumference, by use of a metric ruler. Paws were measured immediately before and at specified time points after carrageenan injection. Inhibitory activity was calculated at 1-5 h after carrageenan injection with the following formula:

% Inhibition=[($Ct$–$C0$)control–($Ct$–$C0$)treated]/($Ct$–$C0$)control×100, where $Ct$ is paw size after carrageenan injection and $C0$ is paw size before carrageenan injection.

Measurement of nitric oxide in serum: Nitric oxide concentration in serum of carrageenan challenged mice with or without treatment was determined by the Griess reaction as an indicator of nitric oxide production as previously reported by Prado (2002) [Prado W A, Schiavon V F, Cunha F Q. Dual effect of local application of nitric oxide donors in a model of incision pain in rats. Eur J Pharmacol. 2002; 441:57-65]. Briefly, 100 microlitre of sera and 100 microlitre of Griess reagent (mix of 2% sulphanilamide in 5% phosphoric acid and 0.2% N(1-naphthyl) ethylenediamine hydrochloride) were mixed in 96-well ELISA plate and Absorbance was read at 550 nm. The concentration of nitrite was determined using a standard curve of sodium nitrite.

Results: Effect of A-O complex on carrageenan induced paw inflammation: The anti-inflammatory effect of A-O complex was tested by administering mice intraperitoneally different concentrations of A-O complex (5, 20 and 50 microgram per 100 g body weight) 1 hour before carrageenan challenge to the paw. From FIG. 13, it can be appreciated that the carrageenan control mice showed significant swelling at 1 hour which remained increased at $3^{rd}$ and $5^{th}$ hours post challenge. The mice administered A-O complex showed significant difference in swelling with respect to carrageenan control mice. Mice administered 5 microgram A-O complex per 100 g body weight showed 25%, 48% and 58% reduction in paw edema in comparison to carrageenan control (which was 100%). Mice administered 20 microgram A-O complex per 100 g body weight showed 30%, 60% and 65% reduction in paw edema in comparison to carrageenan control (which was 100%) whilst those administered 50 microgram A-O complex per 100 g body weight showed 30%, 57% and 65% reduction in paw edema as compared to carrageenan control. Positive control showed 78% edema inhibition at 5$^{th}$ hour.

Effect of A-O complex against carrageenan induced nitrite production in serum: The efficacy of A-O complex to reduce nitrite in serum was determined at 3$^{rd}$ hour post carrageenan challenge. It was found that 50 microgram of A-O complex showed maximal efficiency to reduce serum nitrite level during carrageenan induced acute inflammation (FIG. 14).

Summary of results: As depicted in the data above, the A-O complex prepared is a non-toxic peptide complex, which act as a potent immunomodulator and anti-inflammatory agent. This is made evident by studying the effect of the complex in vitro in ConA induced macrophage and microglial (brain macrophage) cells. Under unstimulated conditions, A-O complex elicits MHC-II and CD36 expression in macrophages whilst under activated conditions, A-O complex reduces macrophage activation. The ability of A-O complex to impart an effect are also seen in unrelated cell types like bone cells indicating that A-O complex has diverse potential. The immunomodulatory effect of A-O complex has also been observed under in vivo conditions.

Advantages of the present disclosure: The present disclosure relates to a complex comprising Abeta 1-42 and undercarboxylated osteocalcin, referred to as A-O complex. The complex is non-toxic in nature and has been observed to have anti-inflammatory and immuno-modulatory functions.

We claim:

1. A peptide complex comprising Abeta 1-42 peptide and undercarboxylated osteocalcin (Glu-OC) for modulating inflammation, wherein Abeta 1-42 peptide is represented by SEQ ID NO: 1, and undercarboxylated osteocalcin is represented by SEQ ID NO: 2.

2. The peptide complex as claimed in claim 1, wherein the undercarboxylated osteocalcin is having uncarboxylated glutamic acid residues at positions 17, 21, and 24.

3. The peptide complex as claimed in claim 1, wherein the complex modulates inflammation by modulating the phenotype of activated macrophages or macrophage related cells.

4. The peptide complex as claimed in claim 3, wherein the macrophage related cells is selected from the group consisting of peripheral blood monocyte/macrophages, microglia, dendritic cell and osteoclasts.

5. The peptide complex as claimed in claim 1, wherein modulating inflammation leads to modulation of diseases selected from the group consisting of macrophage activation syndrome, cardiovascular disease, atherosclerosis, systemic lupus erythematosus (SLE), inflammatory diseases of brain, Kawasaki disease, adult-onset Still's disease, immunologic disease, diabetes and obesity.

6. The peptide complex as claimed in claim 1, wherein the complex is used for immunomodulation.

7. The peptide complex as claimed in claim 6, wherein the complex increases the expression of CD36 scavenger protein in macrophages related cell, thereby leading to immunomodulation.

8. The peptide complex as claimed in claim 6, wherein the complex increases the expression of Major Histocompatibility complex class II molecules, thereby leading to immunomodulation.

9. A composition comprising the peptide complex as claimed in claim 1, and at least one pharmaceutically acceptable excipient or carrier.

10. A method of treating a subject having inflammation, said method comprising, administering to the subject a therapeutically effective amount of the peptide complex as claimed in claim 1.

11. A method of treating a subject having inflammation, said method comprising, administering to the subject a therapeutically effective amount of the composition as claimed in claim 9.

* * * * *

```
                        SEQUENCE LISTING

<160> NUMBER OF SEQ ID NOS: 2

<210> SEQ ID NO 1
<211> LENGTH: 42
<212> TYPE: PRT
<213> ORGANISM: Artificial Sequence
<220> FEATURE:
<223> OTHER INFORMATION: Amino acid sequence of Abeta1-42 peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 49
<212> TYPE: PRT
<213> ORGANISM: Artificial Sequence
<220> FEATURE:
<223> OTHER INFORMATION: Amino acid sequence of undercarboxylated
      osteocalcin

<400> SEQUENCE: 2

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val
```